(12) United States Patent
Campalans et al.

(10) Patent No.: US 10,143,763 B2
(45) Date of Patent: Dec. 4, 2018

(54) NEUTRAL ATMOSPHERE AND SANITIZATION STORAGE APPARATUS, METHOD AND SYSTEM

(71) Applicants: Alfonso Campalans, Houston, TX (US); Alexander Gray, Houston, TX (US)

(72) Inventors: Alfonso Campalans, Houston, TX (US); Alexander Gray, Houston, TX (US)

( * ) Notice: Subject to any disclaimer, the term of this patent is extended or adjusted under 35 U.S.C. 154(b) by 0 days.

(21) Appl. No.: 15/703,903

(22) Filed: Sep. 13, 2017

(65) Prior Publication Data

US 2018/0099062 A1    Apr. 12, 2018

Related U.S. Application Data

(63) Continuation-in-part of application No. 15/287,375, filed on Oct. 6, 2016, now Pat. No. 9,792,748.

(51) Int. Cl.
| | |
|---|---|
| *A61L 2/20* | (2006.01) |
| *B65D 81/20* | (2006.01) |
| *G07C 9/00* | (2006.01) |
| *F24F 110/20* | (2018.01) |
| *F24F 11/30* | (2018.01) |
| *F24F 110/74* | (2018.01) |
| *F24F 110/10* | (2018.01) |
| *F25D 1/00* | (2006.01) |
| *H04L 29/08* | (2006.01) |
| *H04W 4/80* | (2018.01) |

(52) U.S. Cl.
CPC .......... *A61L 2/202* (2013.01); *B65D 81/2076* (2013.01); *G07C 9/00896* (2013.01); *F24F 11/30* (2018.01); *F24F 2110/10* (2018.01); *F24F 2110/20* (2018.01); *F24F 2110/74* (2018.01); *F25D 1/00* (2013.01); *G07C 2009/0092* (2013.01); *H04L 67/12* (2013.01); *H04W 4/80* (2018.02)

(58) Field of Classification Search
CPC ............................ A61L 2/202; B65D 81/2076
See application file for complete search history.

(56) References Cited

U.S. PATENT DOCUMENTS

| | | |
|---|---|---|
| 2,606,122 A | 8/1952 | Stark |
| 2,816,036 A | 12/1957 | Lederer |

(Continued)

*Primary Examiner* — Sean E Conley
(74) *Attorney, Agent, or Firm* — Sean Christian Connolly

(57) ABSTRACT

Disclosed herein are an apparatus, method and system for storing perishable items that degrade in the presence of oxygen and/or humidity and that are frequently accessed by a consumer. The apparatus comprises an openable insulated vessel with precisely controlled internal temperature and humidity, which becomes airtight when closed, and a corona ozone generator with an oxygen gas feed tank and fan within the insulated airtight enclosure, which converts ambient oxygen trapped within the airtight enclosure into ozone by circulating the enclosed volume of air through the corona ozone generator after the vessel is opened and then closed. Also disclosed is a refrigerated embodiment of the apparatus, which may be self-contained and transportable. The apparatus is network connected to allow for remote control and monitoring and sends alerts to web applications or mobile applications when monitored parameters substantially vary from their settings.

30 Claims, 24 Drawing Sheets

(56) References Cited

U.S. PATENT DOCUMENTS

| | | |
|---|---|---|
| 3,060,035 A | 10/1962 | Berst |
| 3,105,764 A | 10/1963 | Wagner |
| 3,865,733 A | 2/1975 | Taylor |
| 3,921,002 A | 11/1975 | Williams et al. |
| 3,967,131 A | 6/1976 | Slipiec et al. |
| 4,051,045 A | 9/1977 | Yamamoto et al. |
| 4,156,652 A | 5/1979 | Wiest |
| 4,772,480 A | 9/1988 | Yamane |
| 5,034,198 A | 7/1991 | Kaiga et al. |
| 5,094,822 A | 3/1992 | Dunder |
| 5,269,146 A | 12/1993 | Kerner |
| 5,316,741 A | 5/1994 | Sewell et al. |
| 5,361,587 A | 11/1994 | Hoffman |
| 5,405,631 A | 4/1995 | Rosenthal |
| 5,427,693 A | 6/1995 | Mausgrover et al. |
| 5,433,927 A | 7/1995 | Mausgrover et al. |
| 5,516,493 A | 5/1996 | Bell et al. |
| 5,575,835 A | 11/1996 | Bailey et al. |
| 5,578,280 A | 11/1996 | Kazi et al. |
| 5,587,131 A | 12/1996 | Malkin et al. |
| 5,603,220 A | 2/1997 | Seaman |
| 5,759,497 A | 6/1998 | Kuzumoto et al. |
| 5,887,435 A | 3/1999 | Morton |
| 5,942,196 A | 8/1999 | Tabata et al. |
| 5,945,073 A | 8/1999 | Ditzler et al. |
| 5,951,921 A | 9/1999 | Koganezawa et al. |
| 5,997,702 A | 12/1999 | Koganezawa et al. |
| 6,058,718 A | 5/2000 | Forsberg et al. |
| 6,082,115 A | 7/2000 | Strnad |
| 6,105,659 A | 8/2000 | Pocol et al. |
| 6,120,822 A | 9/2000 | Denvir et al. |
| 6,132,629 A | 10/2000 | Boley |
| 6,226,958 B1 | 5/2001 | West et al. |
| 6,289,678 B1 | 9/2001 | Pandolfi |
| 6,382,762 B1 | 5/2002 | Therien |
| 6,387,430 B1 | 5/2002 | Gillette et al. |
| 6,455,017 B1 | 9/2002 | Kasting et al. |
| 6,528,022 B1 | 3/2003 | Kinoshita |
| 6,685,549 B2 | 2/2004 | Henry et al. |
| 6,725,598 B2 | 4/2004 | Yoneda et al. |
| 6,942,834 B2 | 9/2005 | Gutman |
| 7,082,772 B2 | 8/2006 | Welch |
| 7,118,852 B2 | 10/2006 | Purdum |
| 7,703,291 B2 | 4/2010 | Bushnik et al. |
| 7,817,423 B2 | 10/2010 | Morehead |
| 8,017,074 B2 | 9/2011 | Arnold et al. |
| 8,062,500 B2 | 11/2011 | Sumita |
| 8,278,628 B2 | 10/2012 | Hamilton |
| 8,349,253 B2 | 1/2013 | Gutman |
| 8,425,837 B2 | 4/2013 | Carbone et al. |
| 8,540,943 B2 | 9/2013 | Kee et al. |
| 8,617,479 B2 | 12/2013 | Gil et al. |
| 8,721,984 B2 | 5/2014 | Carbone et al. |
| 8,754,385 B1 | 6/2014 | Gutman |
| 8,808,622 B2 | 8/2014 | Arnold et al. |
| 2001/0046459 A1 | 11/2001 | St. Onge et al. |
| 2003/0108460 A1 | 6/2003 | Andreev et al. |
| 2003/0156978 A1* | 8/2003 | Gillette ............... A23L 3/358 422/31 |
| 2006/0049738 A1 | 3/2006 | Tabata et al. |
| 2007/0165784 A1 | 7/2007 | Nakanishi et al. |
| 2007/0272290 A1 | 11/2007 | Sims et al. |
| 2008/0099122 A1 | 5/2008 | Andersen et al. |
| 2009/0252646 A1 | 10/2009 | Holden et al. |
| 2009/0272279 A1* | 11/2009 | Kieck ............... A47J 47/10 99/468 |
| 2009/0274577 A1 | 11/2009 | Sorensen et al. |
| 2009/0304810 A1 | 12/2009 | Martin |
| 2010/0192987 A1 | 8/2010 | Steffen |
| 2011/0268850 A1 | 11/2011 | Rasanayagam et al. |
| 2012/0021075 A1 | 1/2012 | Umanskaya et al. |
| 2012/0198870 A1 | 8/2012 | Erbs et al. |
| 2012/0230879 A1 | 9/2012 | Dunkley et al. |
| 2014/0287068 A1 | 9/2014 | Lewis et al. |
| 2014/0342124 A1 | 11/2014 | Zambrzycki et al. |

* cited by examiner

FIG. 18
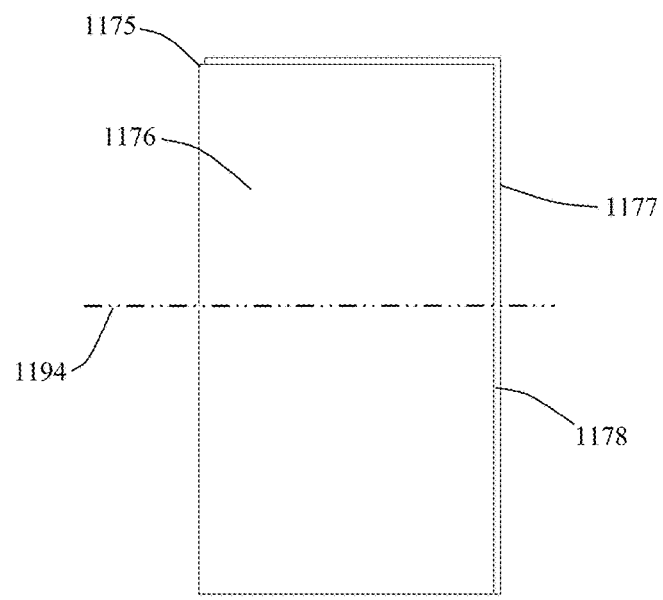
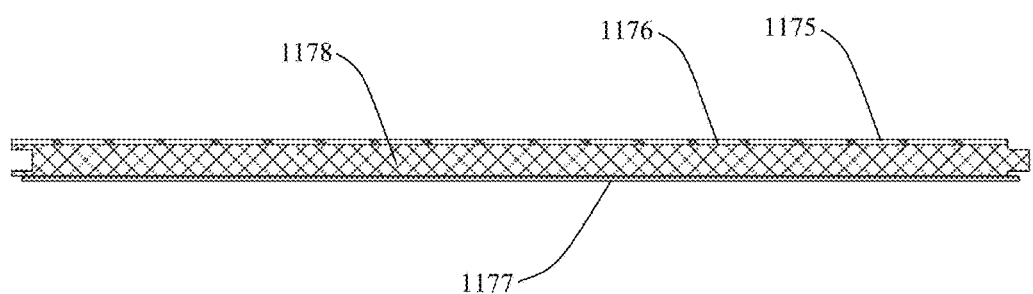

US 10,143,763 B2

NEUTRAL ATMOSPHERE AND SANITIZATION STORAGE APPARATUS, METHOD AND SYSTEM

CROSS-REFERENCE TO RELATED APPLICATIONS

This application is a continuation-in-part of U.S. Utility patent application Ser. No. 15/287,375, which was filed on Oct. 6, 2016, and which is incorporated herein in its entirety.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable

BACKGROUND OF THE INVENTION

1. Field of the Invention

The present invention is in the technical field of containers. More particularly, the preferred embodiments of the present invention relate generally to storage containers. More particularly, the preferred embodiments of the present invention relate generally to storage container for perishable items. More particularly, the preferred embodiments of the present invention relate generally containers for perishable items that degrade when exposed to certain temperatures and/or humidity. More particularly, the preferred embodiments of the present invention relate generally to storage containers for perishable items that degrade over time when exposed to oxygen due to natural decay. More particularly, the preferred embodiments of the present invention relate generally to storage containers for perishable items that degrade when exposed to oxygen, which are frequently accessed. More particularly, the preferred embodiments of the present invention relate generally to frequently accessed storage containers for perishable items that degrade when exposed to oxygen, which use ozone. More particularly, the preferred embodiments of the present invention relate generally to frequently accessed storage containers for perishable items that degrade when exposed to oxygen, which generate ozone. More particularly, the preferred embodiments of the present invention relate generally to frequently accessed storage containers for perishable items that degrade when exposed to oxygen, which generate ozone using corona ozone generation, as well as related methods and systems.

2. Description of the Related Art

The broad concept of storing products in a modified atmosphere is also known. However, these inventions usually involve injecting a modified atmosphere into packaging during manufacturing and are unable to replenish the modified atmosphere once the packaging seal is broken and are not well suited for frequently accessed items.

The broad concept of sanitization processes that use ozone is known. These sanitization processes often involve one-time treatment and are not well suited for repeatedly sanitizing items that are frequently used using gaseous applications.

It is also known to use sanitization processes that generate ozone using corona ozone generation. However, these sanitation processes are not incorporated into storage containers that allow for frequent access and frequent sanitation.

SUMMARY OF THE INVENTION

Particular problems arise in the commercialization of perishable items that degrade in the presence of oxygen, including issues with storage and transportation. Similar issues arise with perishable items that are prone to fungal growth in humid environments. Perishable items that are frequently used by consumers experience increased exposure to oxygen (02) and/or humid environments each time that the perishable items are accessed and removed from their storage container. This increased exposure can accelerate degradation in the quality of the perishable items. Similarly, stress during transportation, including exposure to oxygen, humidity, temperature, and pressure variances, can reduce the quality of perishable items, which has a negative impact on their value. Because of these susceptibilities, the challenge presented is to develop a method, system and apparatus for storing perishable items, which would allow for regular and frequent access, as well as long-term storage and transportation, while maintaining high quality, and while providing for integrated monitoring, tracking and reporting.

In broad embodiment, the present invention relates to storage containers for storing perishable items that degrade in the presence of oxygen, humidity and/or certain temperature ranges, and that are frequently accessed by a consumer; which comprise an insulated and openable vessel, which becomes airtight when closed, a corona ozone generator with an oxygen gas feed and fan within the insulated airtight enclosure, which converts ambient oxygen trapped within the airtight enclosure into ozone by circulating the enclosed volume of air through the corona ozone generator after the vessel is opened and then closed and which increased the ozone levels by feeding oxygen gas into the corona ozone generator; as well as, methods and systems for using the same. Additionally, the present invention incorporates the use and control of dynamic humidity control systems and temperature control systems, which can be monitored and controlled to optimize the conditions for storage of the particular biomass.

In more preferred embodiments, the present invention relates to storage containers for storing perishable items that degrade in the presence of oxygen and/or humidity and that are frequently accessed by a consumer; which comprise an insulated and openable vessel that becomes airtight when closed, a processor module, a corona ozone generator with an oxygen gas feed, a fan, and one or more sensors within the airtight enclosure; as well as, methods and systems for using the same. The one or more sensors in the airtight enclosure relay data measured from the atmosphere within the airtight vessel, such as temperature, humidity, pressure, weight of the perishable items, time of last access (such as the last time the airtight vessel was opened and closed), ozone saturation, or the like, to the processor module, and, when the data measured within the insulated airtight vessel meet specified conditions, the processor module in turn activates the corona ozone generator and fan, hereinafter referred to as the ozone generation cycle or ozone saturation process, thereby converting ambient oxygen trapped within the airtight enclosure into ozone by circulating the enclosed volume of air through the corona ozone generator, until the one or more sensors relay data to the processor module that indicates conditions within the airtight vessel are appropriately sanitized, at which time the processor module deactivates the corona ozone generator and fan until the next time the one or more sensors trigger another ozone generation cycle.

In more preferred embodiments, the present invention relates to an apparatus for storing perishable items that are frequently accessed the apparatus comprising: an outer shell assembly, the outer shell assembly comprising lockable access doors and an exterior indicator; an insulated exposure chamber, the exposure chamber being able to be accessed through the access doors and the exposure chamber being airtight when the access door is closed, the exposure chamber comprising veneer panels within the exposure chambers made of limestone, mahogany, a neutral composite material, or like critical material; an electronics chamber, the electronics chamber comprising a vent to the exterior of the outer shell assembly; a memory stored in non-transitory computer-readable medium, the memory comprising tables of optimal ozone saturation for the perishable items, optimal temperature levels for the perishable items and optimal humidity for the perishable items; a processor module, the processor module enclosed within the electronics chamber and the processor module capable of wireless communication, the processor module capable of controlling the locking or unlocking of the access door, the processor module comprising the computer-readable medium; a power supply module, the power supply module enclosed within the electronics chamber; a corona ozone generator with an oxygen gas feed, the a corona ozone generator with an oxygen gas feed enclosed within the exposure chamber and the a corona ozone generator with an oxygen gas feed being controllable by the processor module; perforated baskets for storing the perishable items, the perforated basket enclosed within the exposure chamber and the perforated basket being sufficiently perforated to allow substantial air flow around the perishable items stored on the perforated basket; a fan, the fan enclosed within the exposure chamber and the fan controllable by the processor module; a temperature sensor, the temperature sensor enclosed within the exposure chamber and the temperature sensor being able to send measured temperature data to the processor module; a humidity sensor, the humidity sensor enclosed within the exposure chamber and the humidity sensor being able to send measured humidity data to the processor module; an ozone sensor, the ozone sensor enclosed within the exposure chamber and the ozone sensor being able to send measured ozone data to the processor module; a temperature control unit, the temperature control unit enclosed within the exposure chamber and the temperature control unit controllable by the processor module; a humidity control unit, the humidity control unit enclosed within the exposure chamber and the humidity control unit controllable by the processor module; wherein the apparatus receives the perishable items on to the perforated basket while the access door is open; the processor module locks the access door, thereby making the exposure chamber airtight; the processor module receives the measured temperature data from the temperature sensor; the processor module receives the measured humidity data from the humidity sensor; the processor module receives the measured ozone data from the ozone sensor; the processor module accesses the tables in the memory and retrieves a recipe based on the perishable items, the measured temperature data, the measured humidity data, and the measured ozone data; and the processor module activates the humidity control unit to achieve the optimal humidity for the perishable items; and the processor module activates the temperature control unit to achieve the optimal temperature for the perishable items; and the processor module activates the corona ozone generator with an oxygen gas feed and the fan, for a time based on retrieved the recipe, to circulate ambient air within the exposure chamber through the corona ozone generator in order to generate ozone within the exposure chamber in an amount sufficient to achieve the optimal ozone saturation and to substantially preserve the quality of the perishable items.

In more preferred embodiments, the present invention also relates to a method of storing, curing, and preserving perishable items that are frequently accessed, the method comprising: obtaining fresh perishable items; providing a memory stored in non-transitory computer-readable medium; the memory comprising tables of optimal ozone saturation for the perishable items, optimal temperature levels for the perishable items and optimal humidity for the perishable items; providing a processor module, the processor module comprising the memory and the processor module being capable of wireless communication; enclosing the perishable items on a perforated basket within an insulated airtight container along with a corona ozone generator, an oxygen gas feed, veneer panels, a fan, a temperature sensor, a humidity sensor, an ozone sensor, a temperature control unit, and a humidity control unit; the corona ozone generator, the oxygen gas feed, the temperature control unit, the humidity control unit, and the fan being controllable by the processor module; the temperature sensor being capable of sending measured temperature data to the processor module; the humidity sensor being capable of sending measured humidity data to the processor module; and the ozone sensor being capable of sending measured ozone data to the processor module; identifying the perishable items to the processor module; measuring the temperature within the insulated airtight container with the temperature sensor; sending the measured temperature data to the processor module; measuring the humidity within the airtight container with the humidity sensor; sending the measured humidity data to the processor module; measuring the ozone within the insulated airtight container with the ozone sensor; sending the measured ozone data to the processor module; accessing the tables in the memory with the processor module; converting the measured temperature data, the measured humidity data, and the measured ozone data to a recipe based on the perishable items and the tables with the processor module; activating the corona ozone generator, the oxygen gas feed and the fan, using the processor module, for a time based on the recipe; activating the temperature control unit for a time based on the recipe; activating the humidity control unit for a time based on the recipe; and circulating ambient air within the exposure chamber around the corona ozone generator in order to generate ozone within the insulated airtight container in an amount sufficient to achieve the optimal ozone saturation and to substantially preserve the quality of the perishable items.

In the most preferred embodiments, the present invention relates to an apparatus, method and system for storing perishable items that degrade in the presence of oxygen and/or humidity, which comprises an openable and lockable outer shell assembly that encloses a processor module, a power supply module, and an insulated inner box assembly with a corona ozone generator with an oxygen gas feed, a combined humidity and temperature sensor, an ozone sensor, a weight sensor, a fan, an inner tray in which to store perishable items, a Peltier heating/cooling element, a humidity control unit, and veneer panels made of a critical material, such as limestone, mahogany, a neutral composite material, or the like. The outer shell assembly comprises a shell body, an outer lid, and a strike lock assembly. The shell body further comprises outer vents, which provide ventilation for the processor module and the power supply module, and is connected to the outer lid by a hinge. The strike lock assembly is capable of locking the outer shell to prevent unauthorized access to the insulated inner box. The processor module is wirelessly networked and capable of connecting to network servers and communicating with web applications and/or applications on mobile platforms, such as smart phones or tablets via Wi-Fi or Bluetooth connections. Further, the processor module is capable of receiving information from the combined humidity and temperature sensor and ozone sensor, directing the locking or unlocking of the outer shell, controlling the opening and closing of the airtight insulated inner box, and coordinating the corona ozone generator with an oxygen gas feed and fan, as well as, the dynamic humidity and temperature modules. Because of the amount of power required to produce ozone and to facilitate the frequent operation of the present invention, the power supply module operates on standard 120 VAC, although those familiar in the art will recognize that more powerful mobile power sources, such as batteries or the like, may be forthcoming. The insulated inner box is openable and airtight when closed and comprises a corona ozone generator with an oxygen gas feed, a combined humidity and temperature sensor, an oxygen sensor, a fan, an inner tray in which to store perishable items, a Peltier heating/cooling element, a humidity control unit, and veneer panels made of a critical material, such as limestone, mahogany, a neutral composite material, or the like. The corona ozone generator is capable of converting ambient oxygen within the airtight inner box into ozone, and additional ozone may be generated by feeding oxygen gas directly into the corona generator (the ozone saturation process) and is capable of being controlled by the processor module. The combined humidity and temperature sensor, the Peltier heating/cooling element and the humidity control unit, monitor and control humidity and temperature to ensure optimum storage conditions. The ozone sensor and the corona ozone generator with an oxygen gas feed, monitor and control ozone levels within the insulated inner box to ensure optimum storage conditions. The weight sensor monitors the weight of the perishable items or biomass being stored to ensure optimum storage conditions. The box sensors and mechanisms relay all data and actions to the processor module, so that the data may be used by the control module, such as turning the corona ozone generator on or off, activating the Peltier heating/cooling element, activating the humidity control unit, sending alerts or status updates, or the like. The fan circulates the ambient air within the inner box in order to maximize its exposure to the corona ozone generator during the ozone saturation process. The inner tray is perforated and holds perishable items within the inner box, so that they are sufficiently exposed to ozone during the ozone saturation process, and stores the perishable items in a region that is readily accessible when the inner lid is open. Some units may replace the indicator light bar with an interactive touch screen control monitor, which is used as a physical end user interface on the unit. This monitor enables the user to check on status, assignment, networking connectivity, and unit access. Additionally, the present invention promotes the proper curing of perishable items or biomass that are stored with in the airtight container.

Still referring to the most preferred embodiment of the present invention, the Improved Neutral Atmosphere and Sanitization Storage Apparatus is primarily controlled through a web application or a mobile application. During use, when the Improved Neutral Atmosphere and Sanitization Storage Apparatus is opened to add or remove perishable items from the inner tray, any ozone contained within the apparatus immediately decays and is replaced by ambient air. Upon closing the Improved Neutral Atmosphere and Sanitization Storage Apparatus, an airtight seal is created within an insulated vessel, which traps ambient air within a previously sanitized space. Generally, the processor module activates the corona ozone generator for a period of time sufficient to convert a substantial amount of the ambient oxygen within the vessel into ozone, and additional ozone may be generated by feeding oxygen gas directly into the corona generator (the ozone saturation process), and automatically turns off the corona ozone generator when the insulated vessel is opened. The time required to convert the oxygen in the vessel into ozone is a calculated period based on the efficiency of the corona ozone generator, the interior volume of the airtight inner box, the type of perishable item, the temperature and humidity within the insulate vessel, and the concentration of ozone desired by the user. The duration and intervals of operation and saturation are all calculated and controlled with firmware keyed to proprietary tables. The ozone saturation process will not reactivate until the user activates it again or within a proprietarily specified number of days from the last opening of the box and adjusted to the specific conditions as set by the user. Germicidal treatments are all pre-calibrated proprietary treatments. Upon the completion of the ozone saturation process, the corona ozone generator will turn off and wait for the next cycle or for the owner to reactivate the ozone saturation process manually. Additionally, a user can customize and define the ozone saturation process cycles as they wish. To set up a customized cycle or activate the ozone saturation process manually, a web application or a mobile application is used, which interacts with the wirelessly networked processor module. After a user initially connects the system and enables network communications, the wirelessly networked processor module automatically seeks out a Wi-Fi network and connects with network servers. The user then creates login information, registers the apparatus, and sets preferences and alert settings for the apparatus. Network servers record settings and begins to monitor the system and maintain diagnostic records on all tracked elements, including, but not limited to, relative humidity, ozone levels, ozone generation cycles, temperature, access (opening/closing) of the system, dynamic humidity cycles run, temperature increases or decreases, or the like. All network encryption keys for end uses are stored by the end user on their systems and not on the network. The Improved Neutral Atmosphere and Sanitization Storage Apparatus provides a cloud-based monitoring system for all diagnostics and alerts generated for all deployed systems. Using a web application on a desktop computer or a mobile application on a smart phone (iOS or android), a user may monitor and/or control various aspects of the Improved Neutral Atmosphere and Sanitization Storage Apparatus, including, but not limited to, opening and closing the lid, locking and unlocking the apparatus, activating humidity or temperature cycles, initiating pre-programmed germicidal treatment cycles, monitoring the temperature and relative humidity (RH) within the airtight enclosure, recording the type of perishable items being stored, displaying or editing a user profile, accessing blogs or FAQs concerning recommendations for storing different types of perishable items, time, setting alerts, displaying the serial number or other identifying information of the apparatus, triggering a hard reset, activating off grid settings, or other custom attributes. A hard switch may reset the hardware and software. Manual activation is also possible when the apparatus is used off grid where wireless network connections are unavailable, and any data that is recorded while the apparatus is off grid is stored and then sent to the network servers when a network connection is later achieved. Some embodiments may comprise direct communication between the web application or the mobile application and the Improved Neutral Atmosphere and Sanitization Storage Apparatus using a Bluetooth connection without changing network defaults for all communications and monitoring, and data collected during direct Bluetooth communications between the application and the Improved Neutral Atmosphere and Sanitization Storage Apparatus are uploaded to the server network. In sum, the Improved Neutral Atmosphere and Sanitation Storage apparatus provides a sophisticated device, which preserves the useful life and quality of perishable items that degrade in the presence of oxygen and/or humidity.

BRIEF DESCRIPTION OF THE DRAWING

Illustrative and preferred embodiments of the present invention are shown in the accompanying drawings in which:

FIG. 18 is a cutaway view of an insulated panel used in the apparatus of FIG. 1 and the apparatus of FIG. 9 of the present invention, showing the interior of the insulated panel;

DETAILED DESCRIPTION OF THE PREFERRED EMBODIMENTS

For the purpose of illustration, the present invention is shown in the preferred embodiments of an apparatus, system and method, for storing perishable items that are frequently accessed, which comprises an insulated vessel, which is airtight when closed; a corona ozone generator with an oxygen gas feed, which is capable of converting ambient oxygen contained within the insulated airtight vessel into ozone; a temperature control unit, which can adjust the temperature within the insulated airtight vessel; a humidity control unit, which can adjust the humidity within the airtight vessel; a sensor array, which measures the conditions within the airtight vessel; a fan; veneer panels within the insulated airtight vessel, which comprise limestone, mahogany, a neutral composite material, or like critical material; and a wirelessly networked processor module, which controls the corona ozone generator, oxygen gas feed, temperature control unit, humidity control unit, and fan, and which automatically turns off the corona ozone generator when the insulated airtight vessel is opened. These embodiments are not intended to limit the scope of the present invention.

Figure 1:
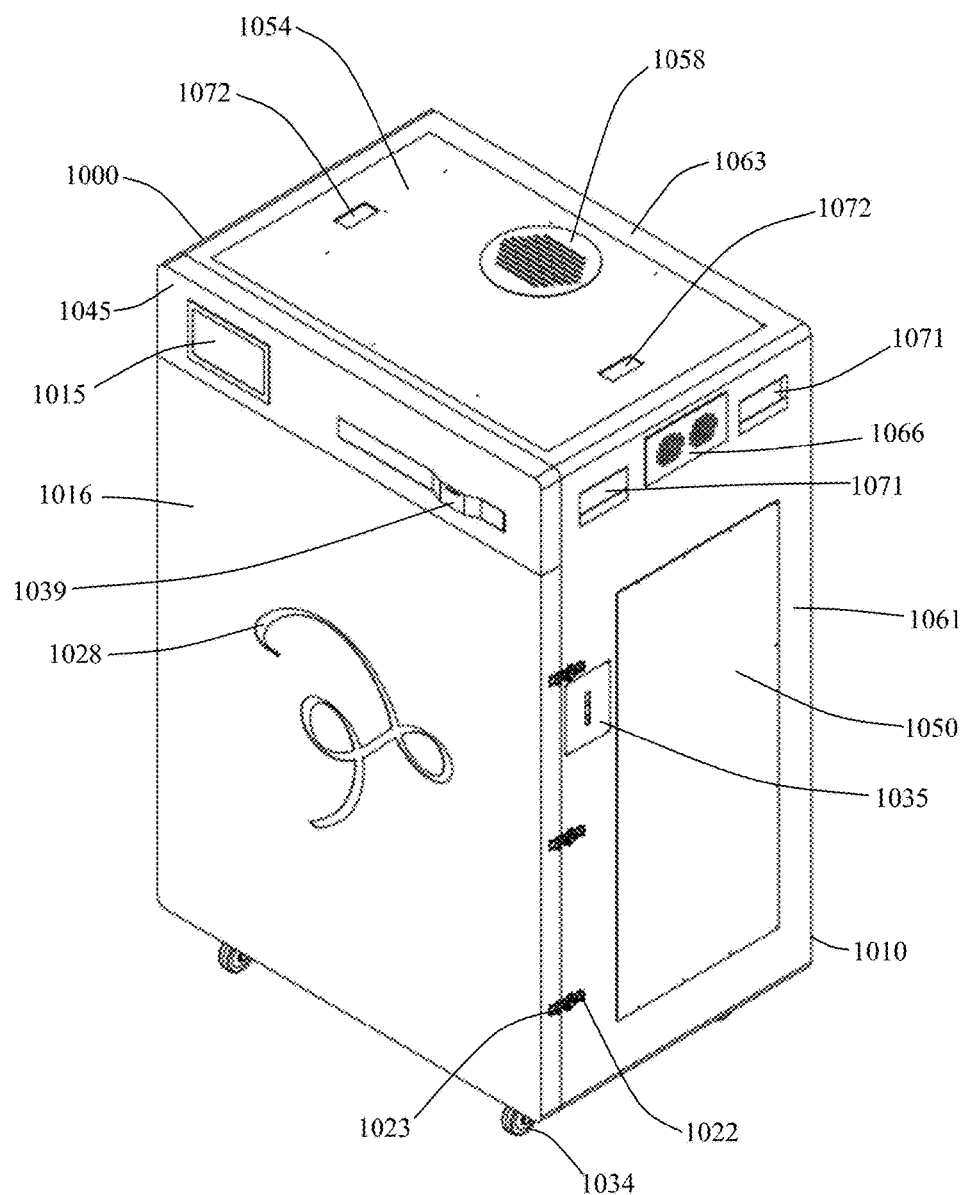
FIG. 1 is a perspective view of the most preferred embodiment of an apparatus of the present invention.
Figure 2:
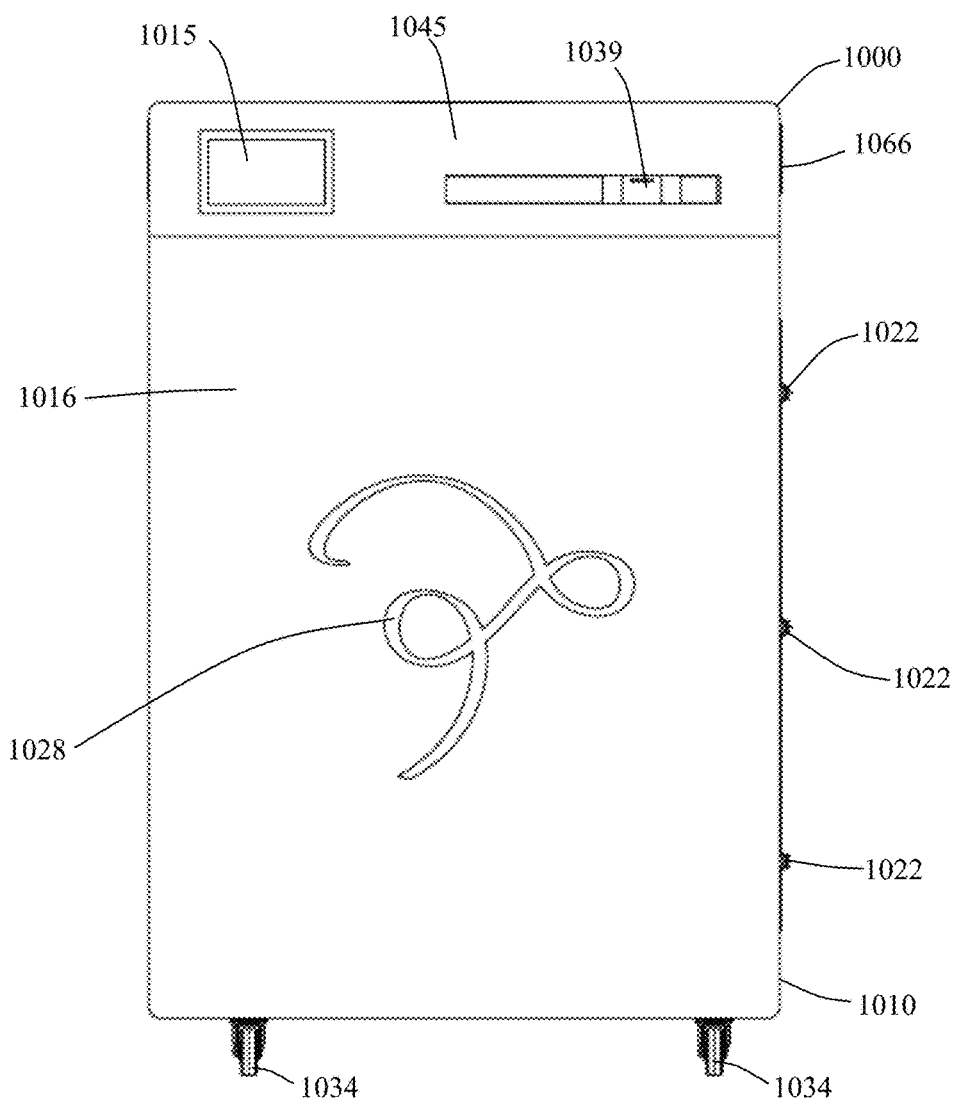
FIG. 2 is a front view of an apparatus of FIG. 1.
Figure 3:
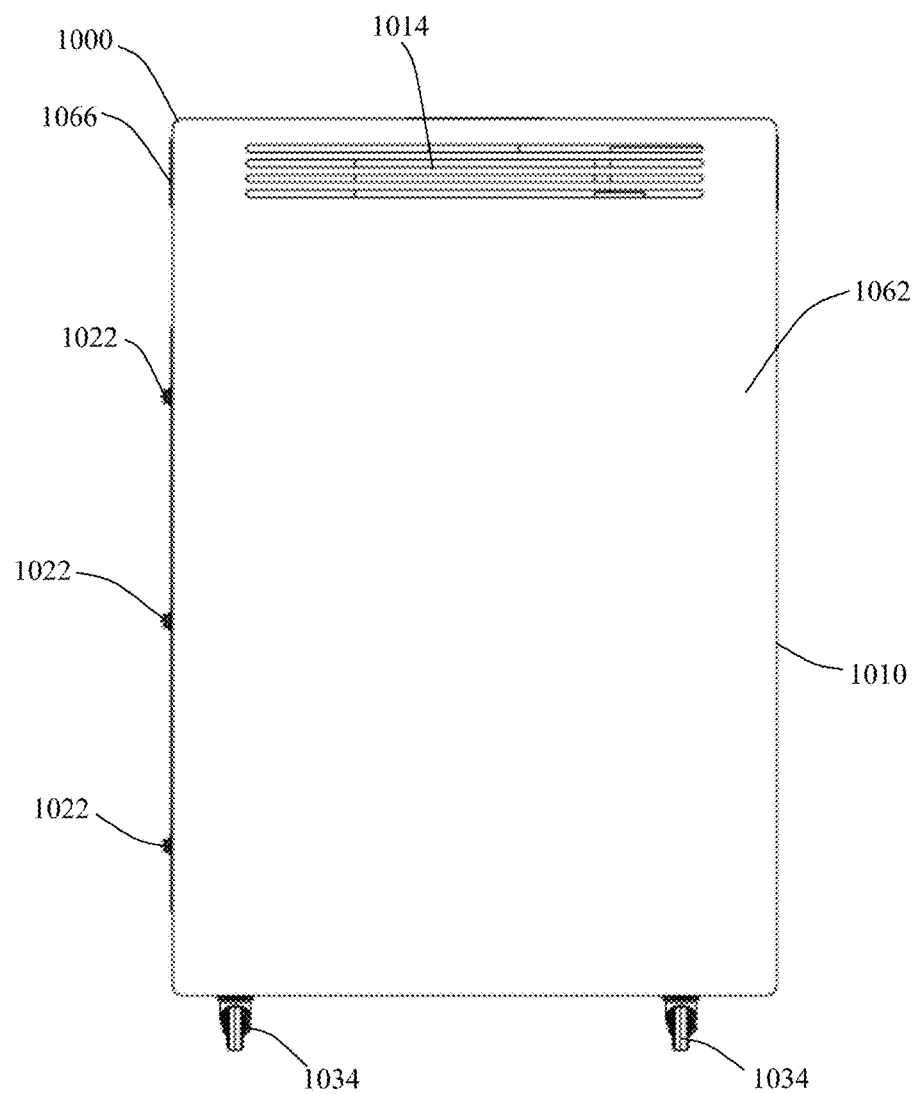
FIG. 3 is a rear view of an apparatus of FIG. 1.
Figure 4:
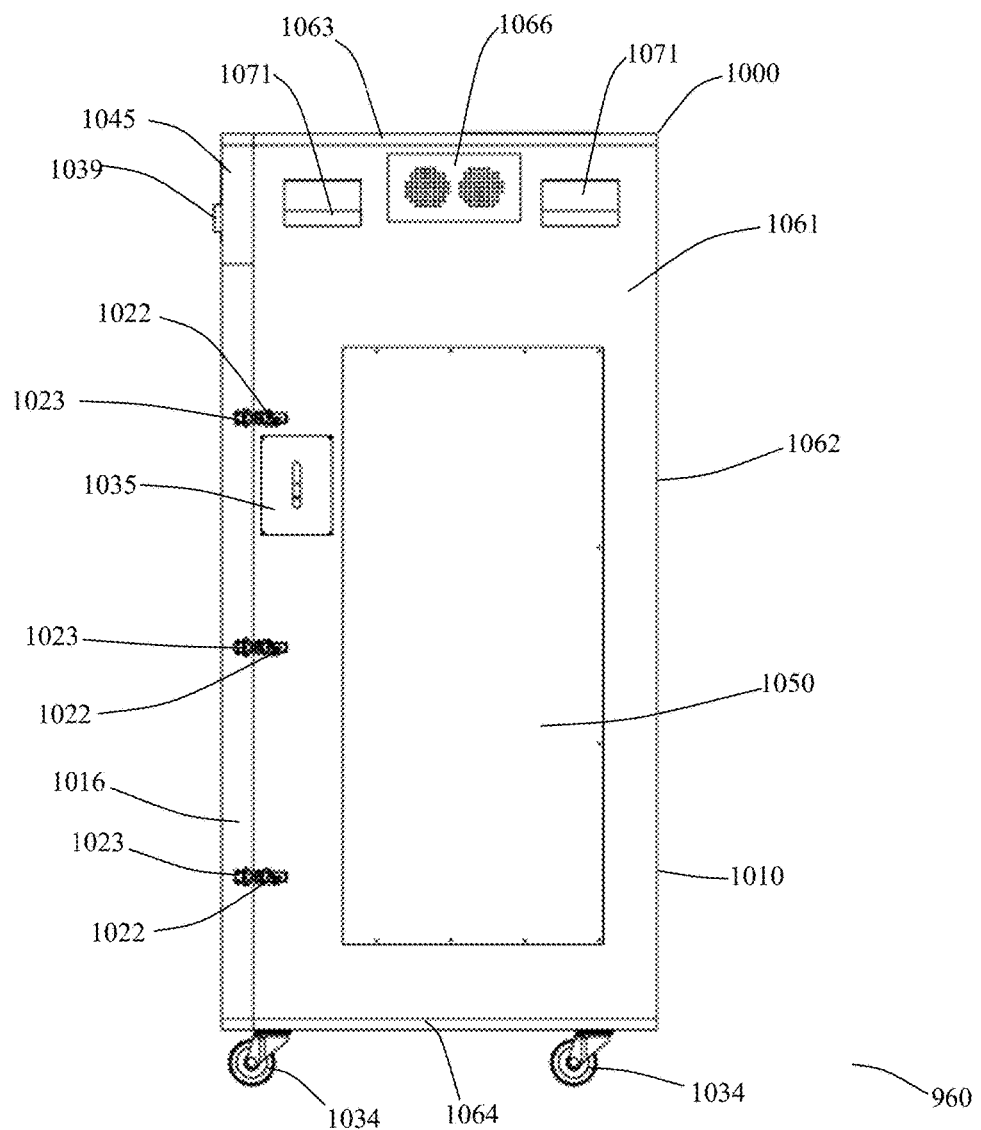
FIG. 4 is a right side view of an apparatus of FIG. 1.
Figure 5:
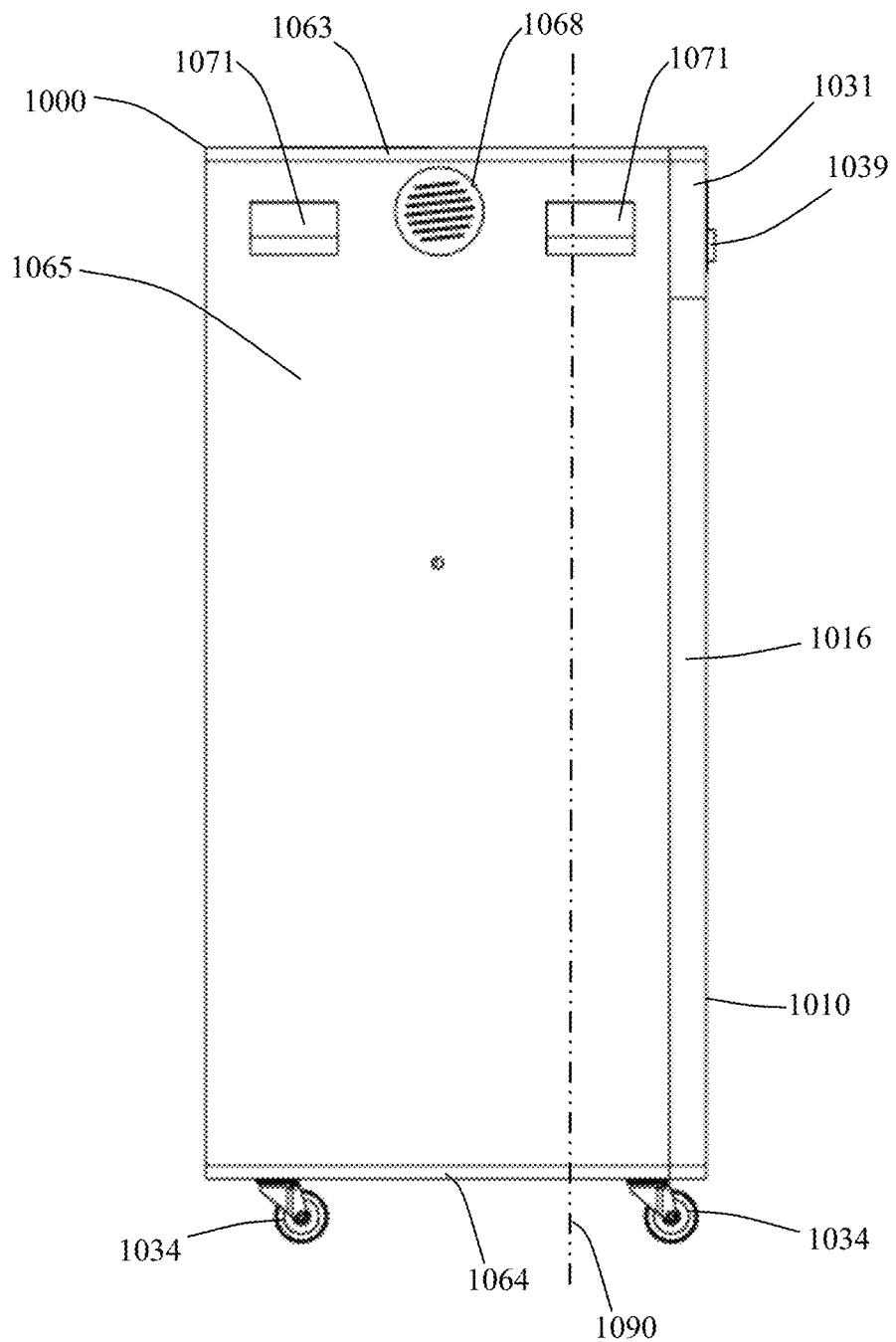
FIG. 5 is a left side view of an apparatus of FIG. 1.
Figure 6:
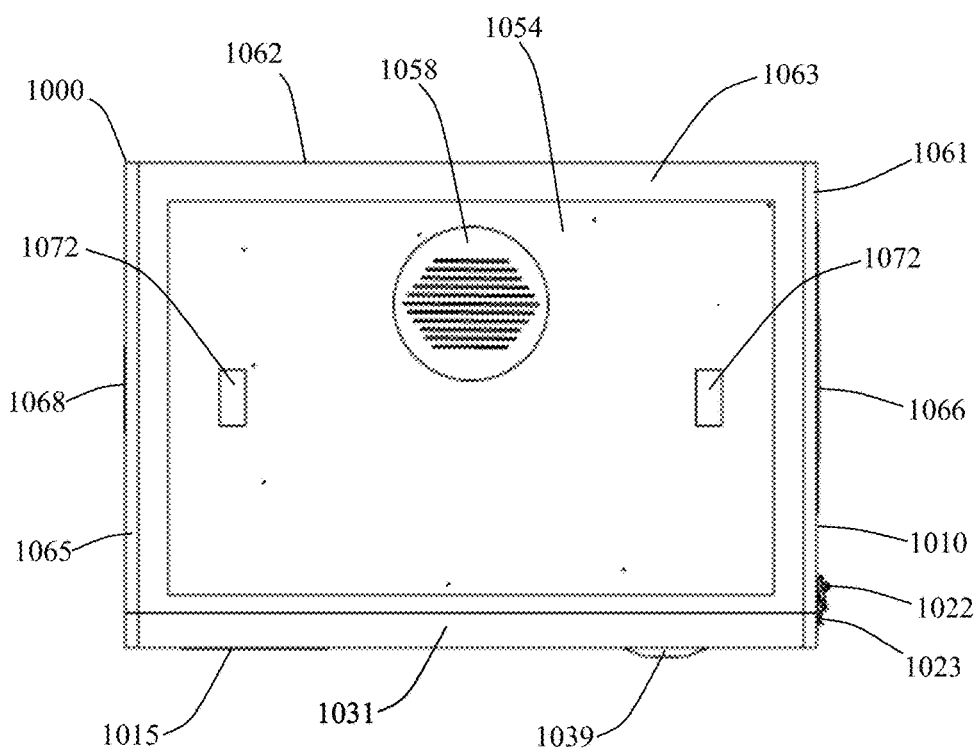
FIG. 6 is a top view of an apparatus of FIG. 1.
Figure 7:
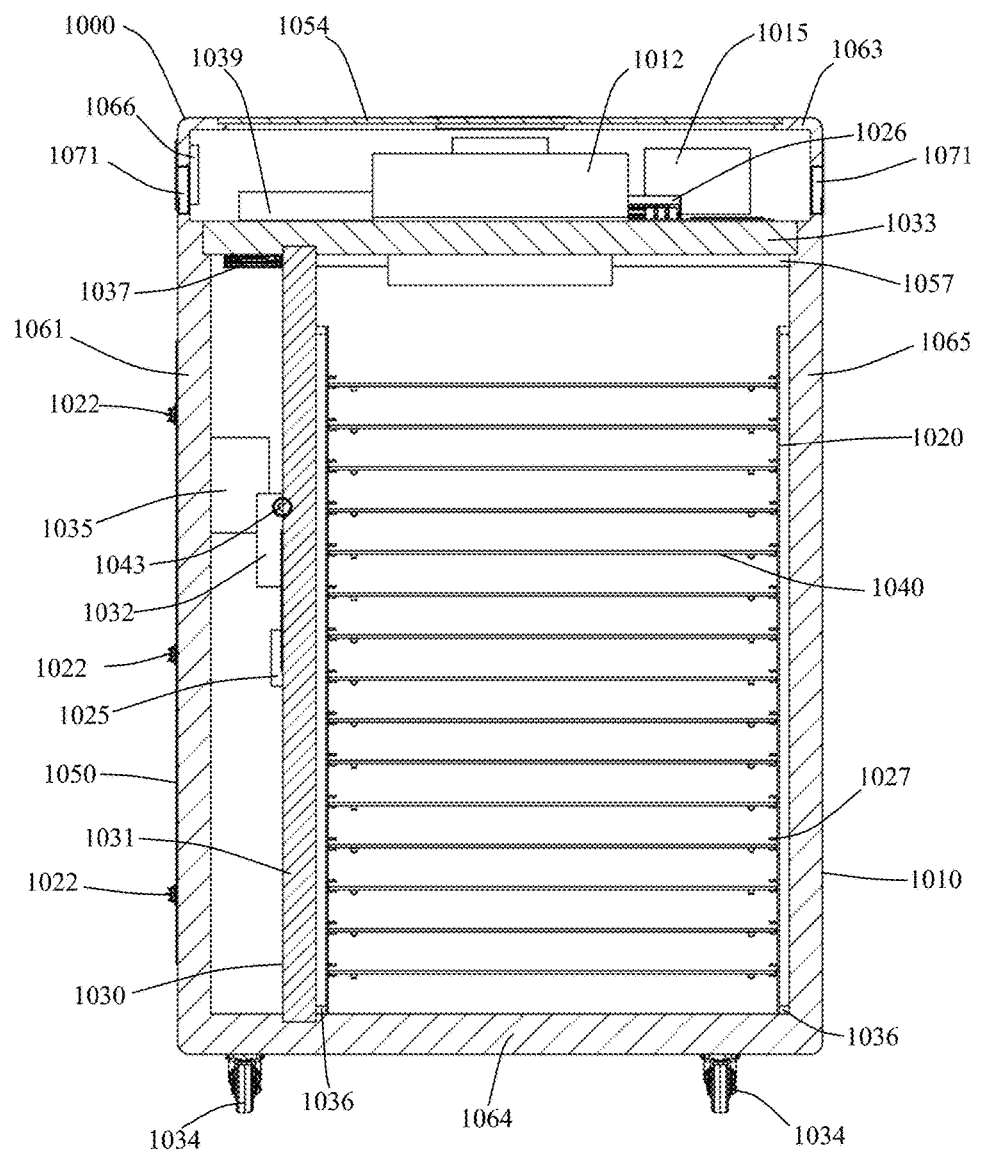
FIG. 7 is a rear cutaway view of an apparatus of FIG. 1, showing the interior of the present invention.
Figure 8:
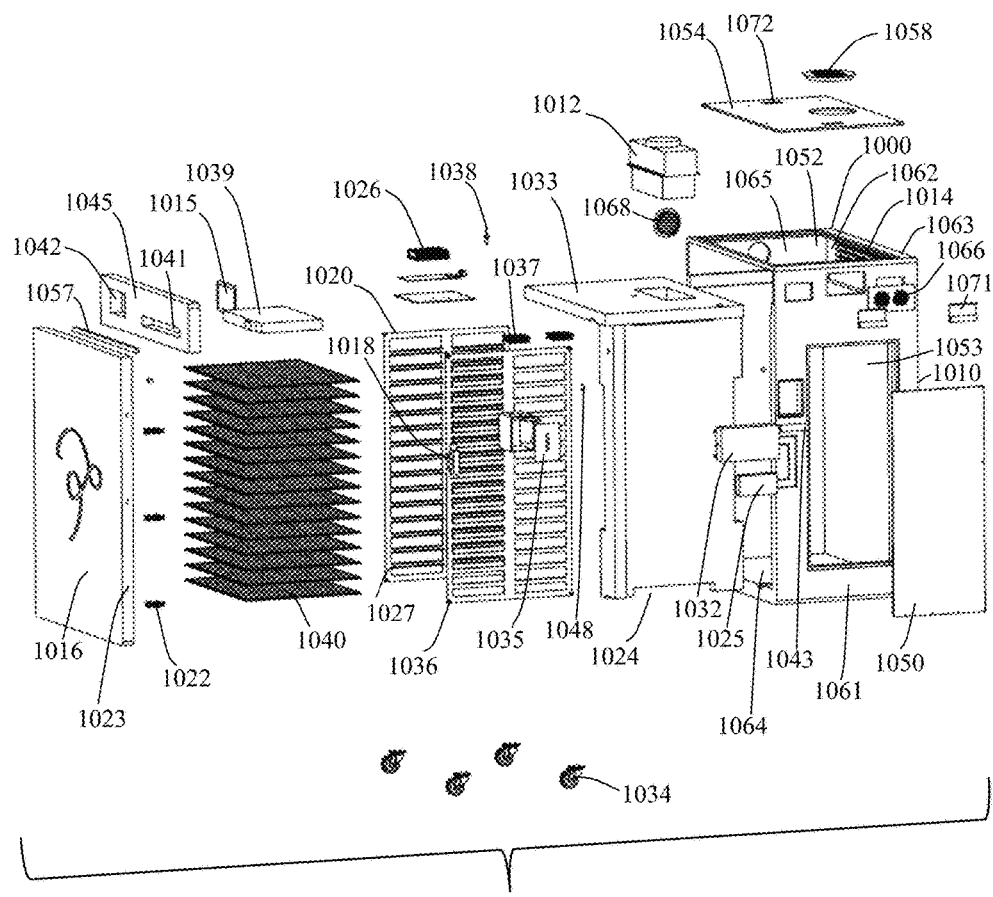
FIG. 8 is an exploded perspective view of an apparatus of FIG. 1.
Figure 19:
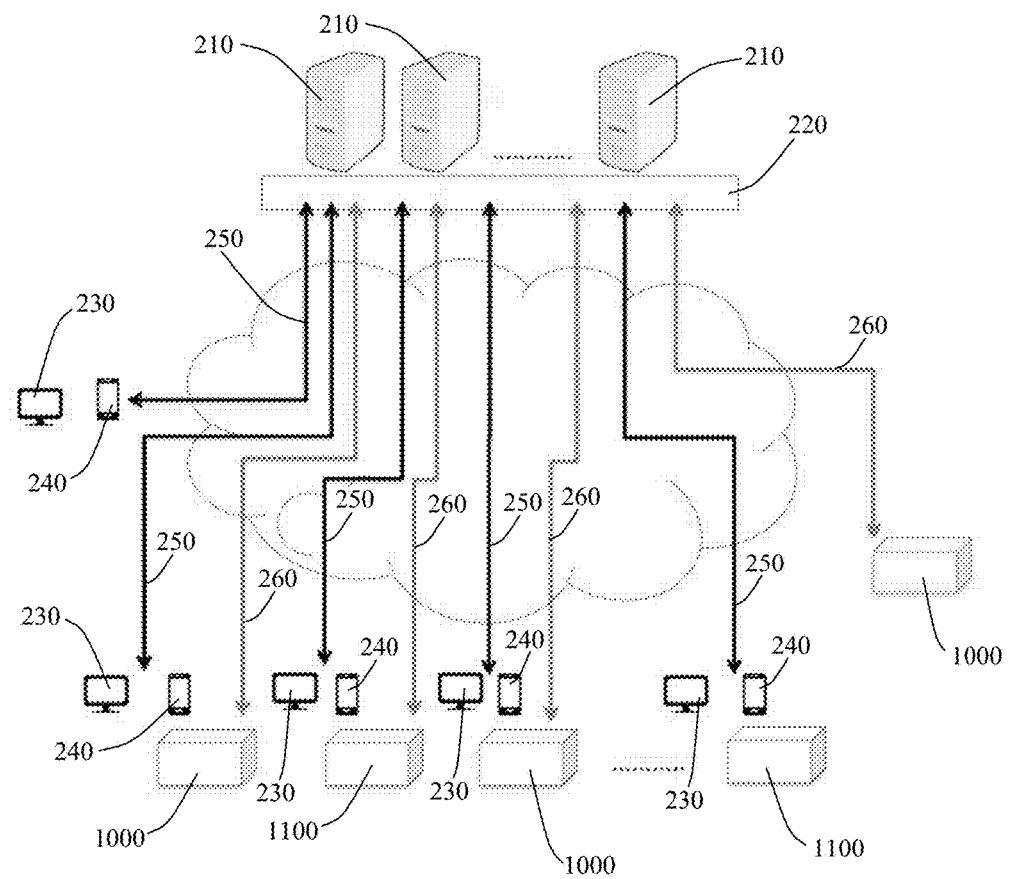
FIG. 19 is a diagram, which describes a preferred embodiment of a network configuration related to the present invention.
Figure 20:
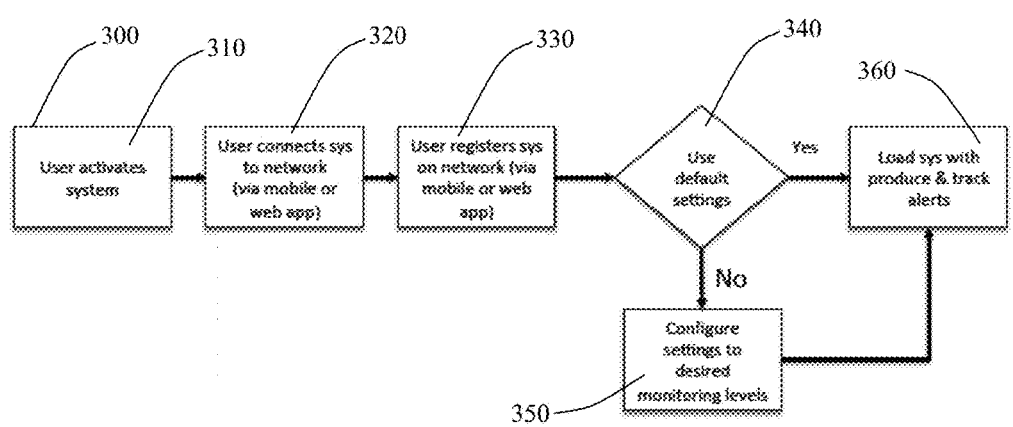
FIG. 20 is a flow chart, which describes the process for setting up and configuring the present invention.
Figure 21:
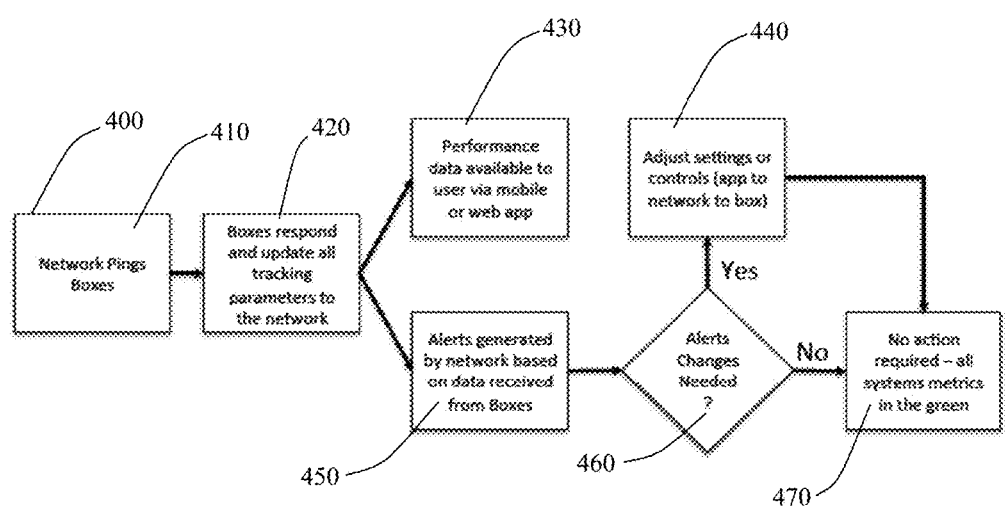
FIG. 21 is a flow chart, which describes the interactions of the software application, server network and the present invention.
Figure 22:
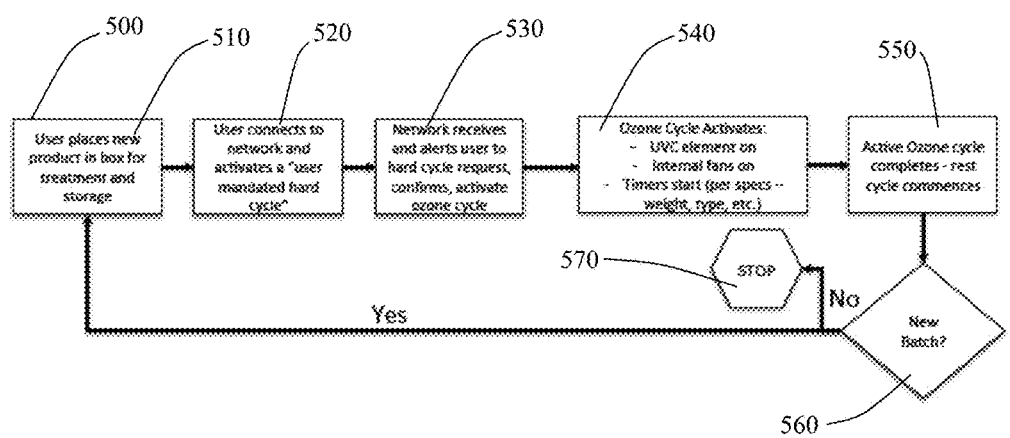
FIG. 22 is a flow chart, which describes the process for the manual operation of the present invention.
Figure 23:
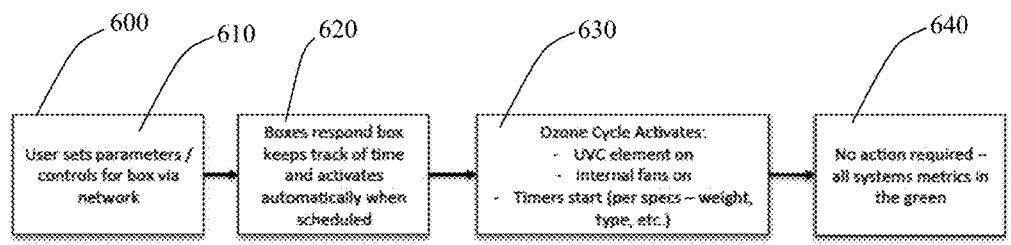
FIG. 23 is a flow chart, which describes the process for the programmed operation of the present invention.
Figure 24:
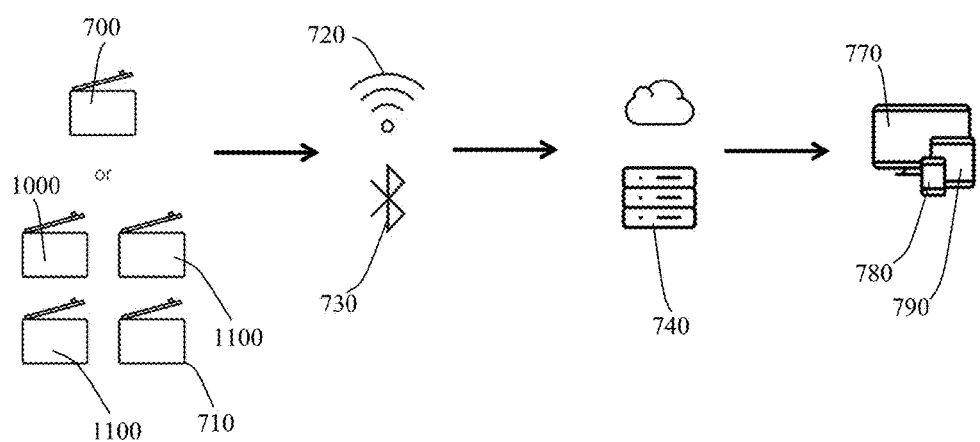
FIG. 24 is a diagram, which describes a most preferred embodiment of a network configuration related to the present invention.

Referring to the most preferred embodiment of the present invention, in FIG. 1, FIG. 2, FIG. 3, FIG. 4, FIG. 5, FIG. 6, FIG. 7, FIG. 8, FIG. 18, FIG. 19, FIG. 20, FIG. 21, FIG. 22, FIG. 23, and FIG. 24, a Pro Plus Neutral Atmosphere and Sanitization Storage Apparatus 1000 is shown. FIG. 1 illustrates a perspective view of a Pro Plus Neutral Atmosphere and Sanitization Storage Apparatus 1000. FIG. 2 depicts a front view of a Pro Plus Neutral Atmosphere and Sanitization Storage Apparatus 1000. FIG. 3 shows a rear view of a Pro Plus Neutral Atmosphere and Sanitization Storage Apparatus 1000. FIG. 4 displays a right side view of a Pro Plus Neutral Atmosphere and Sanitization Storage Apparatus 1000. FIG. 5 shows a left side view of a Pro Plus Neutral Atmosphere and Sanitization Storage Apparatus 1000. FIG. 6 depicts a top view of a Pro Plus Neutral Atmosphere and Sanitization Storage Apparatus 1000. FIG. 7 illustrates a rear cutaway view of a Pro Plus Neutral Atmosphere and Sanitization Storage Apparatus 1000 with the cutaway positioned at the dotted line 1090 in FIG. 5. FIG. 8 demonstrates an exploded perspective view of a Pro Plus Neutral Atmosphere and Sanitization Storage Apparatus 1000. FIG. 18 illustrates a cutaway view of a insulation panel 1175 used in a Pro Plus Neutral Atmosphere and Sanitization Storage Apparatus 1000 with the cutaway positioned at the dotted line 1194, showing the inner insulation 1178, the first outer veneer panel 1176 and second outer veneer panel 1177 of the insulated panel 1175. FIG. 19 displays a diagram, which describes the network configuration related to the Pro Plus Neutral Atmosphere and Sanitization Storage Apparatus 1000. FIG. 20 depicts a flow chart, which describes the process for setting up and configuring the Pro Plus Neutral Atmosphere and Sanitization Storage Apparatus 1000. FIG. 21 shows a flow chart, which describes the interactions of the web application 230, mobile application 240, network servers 210 and the Pro Plus Neutral Atmosphere and Sanitization Storage Apparatus 1000. FIG. 22 illustrates a flow chart, which describes the process for the manual operation of the Pro Plus Neutral Atmosphere and Sanitization Storage Apparatus 1000. FIG. 23 demonstrates a flow chart, which describes the process for the programmed operation of the Pro Plus Neutral Atmosphere and Sanitization Storage Apparatus 1000. FIG. 24 shows a diagram, which describes a most preferred embodiment of a network configuration related to the Pro Plus Neutral Atmosphere and Sanitization Storage Apparatus 1000.

Referring still to the most preferred embodiment of the invention, in FIG. 1, FIG. 2, FIG. 3, FIG. 4, FIG. 5, FIG. 6, FIG. 7, FIG. 8, FIG. 18, FIG. 19, FIG. 20, FIG. 21, FIG. 22, FIG. 23, and FIG. 24, the Pro Plus Neutral Atmosphere and Sanitization Storage Apparatus 1000 comprises an openable and lockable Pro Plus outer shell assembly 1010, an insulated and airtight Pro Plus inner shell assembly 1030, and a Pro Plus exposure chamber cage 1020. The Pro Plus outer shell assembly 1010 comprises a Pro Plus insulated front door 1016, a Pro Plus insulated left side panel 1065, a Pro Plus insulated right side panel 1061, a Pro Plus insulated rear panel 1062, a Pro Plus insulated top panel 1063, a Pro Plus insulated bottom panel 1064, and a Pro Plus electronics cover 1045. The improved insulation in the Pro Plus Neutral Atmosphere and Sanitization Storage Apparatus 1000 allows for improved precision with regards to temperature and humidity control. The Pro Plus insulated front door 1016 comprises a plurality of Pro Plus latch receivers 1023 and is hingedly attached to the Pro Plus insulated left side panel 1065. The Pro Plus insulated left side panel 1065 is hingedly attached to the Pro Plus front door 1016 and comprises two Pro Plus side handles 1071 and a Pro Plus left vent 1068. The Pro Plus insulated right side panel 1061 comprises a Pro Plus precision humidity control unit 1035, Pro Plus dual cooling fans 1066, a Pro Plus side door opening 1053, a Pro Plus insulated side door 1050 that fits into the Pro Plus side door opening 1053, two Pro Plus side handles 1071, a plurality of Pro Plus locking latches 1022 that lockably connect to the plurality of Pro Plus latch receivers 1023 in the Pro Plus front door 1016, and a Pro Plus strike lock 1018, which interacts with the Pro Plus processor module 1026, the Pro Plus latch receivers 1023, and the Pro Plus locking latches 1022 to control the locking and unlocking of the Pro Plus insulated outer shell assembly 1010 to prevent unauthorized access to the Pro Plus Neutral Atmosphere and Sanitization Storage Apparatus 1000. The Pro Plus insulated rear panel 1062 comprises a Pro Plus outer vent 1014, which provides ventilation for the enclosed electronics. The Pro Plus insulated top panel 1063 comprises a Pro Plus top opening 1052 and a Pro Plus top access panel 1054, which fits into the Pro Plus top opening 1052 and provides access to the enclosed electronics. The Pro Plus insulated top access panel 1054 comprises two Pro Plus top handles 1072 and a Pro Plus top vent 1058. The Pro Plus insulated bottom panel 1064 comprises a set of Pro Plus casters 1034 that depend from the bottom of the Pro Plus insulated bottom panel 1064 and allow the Pro Plus Neutral Atmosphere and Sanitization Storage Apparatus 1000 to be transported. The Pro Plus electronics cover 1045 is above the Pro Plus insulated front door 1016 and comprises a Pro Plus UPS access opening 1041, through which the Pro Plus power supply/UPS module 1039 extends, and a Pro Plus touchscreen opening 1042, through which the Pro Plus touchscreen 1015 extends, so that both components may be controlled. The Pro Plus insulated inner shell assembly 1030 comprises a Pro Plus insulated electronics shelf 1033; which provides an airtight barrier enclosing the Pro Plus exposure chamber cage 1020, the Pro Plus corona ozone generator 1032, the Pro Plus corona ozone generator ballast 1025, the Pro Plus oxygen gas feed tank 1043, the Pro Plus combined humidity and temperature sensor 1038, the Pro Plus ozone sensor 1048, the Pro Plus terpene injector 1047, the Pro Plus inner vent 1024, the Pro Plus Peltier heating/cooling element 1012, the Pro Plus humidity control unit 1035, veneer panels 1176, 1177, and a Pro Plus insulated dividing wall 1031. The terpene injector 1047 is capable of infusing any stored perishable items with terpenes and is controllable by the Pro Plus processor module 1026. The veneer panels 1176, 1177 comprise limestone, mahogany, a neutral composite material, or a like critical material, and provide the function of simulating the conditions of a cave for storing or aging cheese or, similarly, a wine cellar for storing wine while maintaining its quality. Further, the veneer panels 1176, 1177 may be incorporated into insulation panels 1175, which comprise inner insulation 1178, a first outer veneer panel 1176 and a second outer veneer panel 1177. Additionally, the Pro Plus insulated front door 1016, Pro Plus insulated left side panel 1065, Pro Plus insulated right side panel 1061, Pro Plus insulated rear panel 1062, Pro Plus insulated top panel 1063, Pro Plus insulated bottom panel 1064, a Pro Plus electronics cover 1045, a Pro Plus insulated side door 1050, Pro Plus insulated inner shell assembly 1030, and Pro Plus insulated electronics shelf 1033 may comprise insulation panels 1175. The Pro Plus Peltier heating/cooling element 1012 combined with the improved insulation provides improved precision for temperature control as well as a wider range of temperature set points, including temperatures appropriate for refrigeration of any particular perishable items being stored within the apparatus and including, but not limited to, freezing temperatures. The Pro Plus insulated electronics shelf 1033 comprises the electronics and provides supports for them. The electronics comprise a Pro Plus touchscreen 1015, a Pro Plus processor module 1026, and a Pro Plus power supply/UPS module 1039. The Pro Plus insulated dividing wall 1031 also comprises the exposure equipment, and provides support for them. The exposure equipment comprise a Pro Plus corona ozone generator 1032 that is attached to the insulated dividing wall 1031, a Pro Plus corona ozone generator ballast 1025 that is attached to the Pro Plus insulated dividing wall 1031, a Pro Plus combined humidity and temperature sensor 1038, a Pro Plus ozone sensor 1048, a Pro Plus Peltier heating/cooling element 1012, a Pro Plus humidity control unit 1035, and a Pro Plus inner vent 1024, which is a space in the Pro Plus insulated dividing wall 1031 that allows air to circulate through the Pro Plus corona ozone generator 1032, the Pro Plus combined humidity and temperature sensor 1038, the Pro Plus ozone sensor 1048, the Pro Plus Peltier heating/cooling element 1012, the Pro Plus humidity control unit 1035 and the Pro Plus exposure chamber cage 1020. The Pro Plus exposure chamber cage 1020 is airtightably enclosed within the Pro Plus inner shell assembly 1030 and comprises a cage comprised of a plurality of Pro Plus u-brackets 1027 that support a plurality of slidable Pro Plus perforated trays 1040, a set of load weight sensors 1036, and a Pro Plus fan 1037, which is attached to the cage. The Pro Plus processor module 1026 is wirelessly networked through a direct Wi-Fi connection 720 or a direct Bluetooth connection 730 and capable of connecting to direct network servers 740 and, through the direct network servers 740, communicating with applications running on personal computers 770, smart phones 780 or tablets 790. Further, the Pro Plus processor module 1026 is capable of receiving information from the Pro Plus combined humidity and temperature sensor 1038, Pro Plus ozone sensor 1048, and the load weigh sensors 1036; directing the locking or unlocking of the Pro Plus front door 1016 by controlling the Pro Plus locking latch 1022, Pro Plus strike lock 1018, and the Pro Plus latch receiver 1023; controlling the Pro Plus touchscreen 1015; and coordinating and dynamically controlling the Pro Plus corona ozone generator 1032, the Pro Plus oxygen gas feed tank 1043, the Pro Plus Peltier heating/cooling element 1012, the Pro Plus humidity control unit 1035 and the Pro Plus fan 1037. Because of the amount of power required to produce ozone and to facilitate the frequent operation of the present invention, the Pro Plus power supply/UPS module 1039 operates on standard 120 VAC and is also capable of providing uninterrupted power supply in case of a power outage. The insulated Pro Plus inner shell assembly 1030 is openable using the Pro Plus front door 1016 and airtight when the Pro Plus front door 1016 is closed. The Pro Plus touchscreen 1015 is controlled by the Pro Plus processor module 1026, and may be used to indicate whether the Pro Plus corona ozone generator 1032 is activated or other useful information about the present invention, such as temperature, humidity, and ozone readings or the contents of the Pro Plus perforated trays 1040 and their weight. The Pro Plus corona ozone generator 1032 is capable of converting ambient oxygen within the Pro Plus inner shell assembly 1030 into ozone (ozone saturation process), as well as supply additional ozone by converting oxygen from the Pro Plus oxygen gas feed tank 1043 into ozone, and is capable of being controlled by the Pro Plus processor module 1026. The plurality of Pro Plus perforated trays 1040 are sufficiently perforated to allow the free flow of air around any perishable item or biomass being stored within the Pro Plus Neutral Atmosphere and Sanitization Storage Apparatus 1000. The Pro Plus combined humidity and temperature sensor 1038 is mounted in close proximity to the Pro Plus perforated trays 1040 and measures humidity and temperature levels within the Pro Plus inner shell assembly 1030 and relays the measured data to the Pro Plus processor module 1026, so that the data may be used to trigger certain actions by the Pro Plus processor module 1026, such as turning the Pro Plus corona ozone generator 1032 on or off, turning the Pro Plus Peltier heating/cooling element 1012 on or off, turning the Pro Plus humidity control unit 1035 on or off, sending one or more alerts, or the like. The Pro Plus ozone sensor 1048 is mounted in close proximity to the Pro Plus perforated trays 1040 and measures ozone levels within the Pro Plus inner shell assembly 1030 and relays the measured data to the Pro Plus processor module 1026, so that the data may be used to trigger certain actions by the Pro Plus processor module 1026, such as turning the Pro Plus corona ozone generator 1032 on or off, turning the Pro Plus Peltier heating/cooling element 1012 on or off, turning the Pro Plus humidity control unit 1035 on or off, sending one or more alerts, or the like. The plurality of load weight sensors 1036 is mounted under the Pro Plus perforated trays 1040 and measures the weight of any perishable item or biomass being stored within the Pro Plus Neutral Atmosphere and Sanitization Storage Apparatus 1000 and relays the measured data to the Pro Plus processor module 1026, so that the data may be used to trigger certain actions by the Pro Plus processor module 1026, such as turning the Pro Plus corona ozone generator 1032 on or off, turning the Pro Plus Peltier heating/cooling element 1012 on or off, turning the Pro Plus humidity control unit 1035 on or off, sending one or more alerts, or the like. The Pro Plus fan 1037 circulates the ambient air within the Pro Plus inner shell assembly 1030 in order to maximize its exposure to the Pro Plus corona ozone generator 1032 during the ozone saturation process. The plurality of Pro Plus perforated trays 1040 holds perishable items or biomass within the Pro Plus inner shell assembly 1030, so that the perishable items or biomass are sufficiently exposed to the air within the Pro Plus inner shell assembly 1030 to benefit from ozone saturation, temperature control, and humidity control, and stores the perishable items or biomass in a region that is readily accessible when the Pro Plus front door 1016 is open.

The construction details of the invention as shown in FIG. 1, FIG. 2, FIG. 3, FIG. 4, FIG. 5, FIG. 6, FIG. 7, FIG. 8, FIG. 18, FIG. 19, FIG. 20, FIG. 21, FIG. 22, FIG. 23, and FIG. 24, are as follows. The Pro Plus outer shell assembly 1010, including the Pro Plus insulated front door 1016, the Pro Plus insulated left side panel 1065, the Pro Plus insulated right side panel 1061, the Pro Plus insulated side door 1050, the Pro Plus insulated rear panel 1062, the Pro Plus insulated top panel 1063, the Pro Plus insulated top access panel 1054, Pro Plus insulated dividing wall 1031, and the Pro Plus electronics cover 1045; and the Pro Plus insulated inner shell assembly 1030, including the Pro Plus insulated electronics shelf 1033, comprise the inner insulation 1178, the first outer veneer panel 1176 and the second outer veneer panel 1177 of the insulated panel 1175 and may also comprise a strong, rigid, durable material, such as aluminum, metal, steel, glass, plastic, polycarbonate, composite material, ceramic, fiberglass, other types of wood, or the like. The veneer panels 1176, 1177 comprise limestone, mahogany, a neutral composite material, or a like critical material, and provide the function of simulating the conditions of a cave for storing or aging cheese or, similarly, a wine cellar for storing wine while maintaining its quality. The inner insulation 1178 comprises composite insulation, cotton, foam, plastic, ceramic, fiberglass, wood, or the like. The Pro Plus power supply/UPS module 1039 comprises a transformer, a 120 VAC power source, an electronic ballast, a battery pack, a uninterrupted power supply (UPS), a solar cell, or the like. The Pro Plus processor module 1026 comprises a compact wirelessly connected computer. The Pro Plus locking latch 1022, Pro Plus strike lock 1018, and the Pro Plus latch receiver 1023, interact with the Pro Plus processor module 1026 and comprises a rigid, durable material such as aluminum, metal, steel, composite material, or the like. The Pro Plus side handles 1071 and the Pro Plus top handles 1072 comprise a strong, rigid, durable material, such as aluminum, metal, steel, glass, plastic, polycarbonate, composite material, ceramic, fiberglass, wood, or the like. The Pro Plus electronics ledge 1057 comprises a strong, rigid, durable material, such as aluminum, metal, steel, glass, plastic, polycarbonate, composite material, ceramic, fiberglass, wood, or the like. The Pro Plus exposure chamber cage 1020, including the Pro Plus u-bracket 1027, comprises a strong, rigid material, such as aluminum, metal, steel, composite material, or the like. The Pro Plus corona ozone generator 1032 comprises a device that generates an electric field in the presence of oxygen, as well as, the electrical connections for the generator. The Pro Plus oxygen gas feed tank 1043 is capable of holding pressurized oxygen gas and feeding the oxygen gas directly to the Pro Plus corona ozone generator 1032 and comprises a strong, rigid, durable material that is resistant to pure oxygen gas, such as metal, steel, glass, composite material, ceramic, or the like. The Pro Plus fan 1037 is a compact electrical component, which interacts with the Pro Plus processor module 1026 and the Pro Plus power supply/UPS module 1039, and comprises a durable material, such as aluminum, metal, steel, plastic, composite material, or the like. The Pro Plus combined humidity and temperature sensor 1038 is a compact electrical component, which interacts with the Pro Plus processor module 1026, and comprises a durable material, such as aluminum, metal, steel, plastic, composite material, or the like. The Pro Plus ozone sensor 1038 is a compact electrical component, which interacts with the Pro Plus processor module 1026, and comprises a durable material, such as aluminum, metal, steel, plastic, composite material, or the like. The Pro Plus humidity control unit 1035 is a compact electrical component, which interacts with the Pro Plus processor module 1026 and the Pro Plus power supply/UPS module 1039, which may comprise a humidifier and a dehumidifier, and comprises a durable material, such as aluminum, metal, steel, plastic, composite material, or the like. The Pro Plus Peltier heating/cooling element 1012 is a compact electrical component comprising a solid-state Peltier device, which generates heat or provides cooling by removing heat, which interacts with the Pro Plus processor module 1026 and the Pro Plus power supply/UPS module 1039, and comprises a durable material, such as aluminum, metal, steel, plastic, composite material, or the like. The Pro Plus touchscreen 1015 is a compact electrical component, which interacts with the Pro Plus processor module 1026 and the Pro Plus power supply/UPS module 1039, and comprises a durable material, such as aluminum, metal, steel, glass, plastic, composite material, or the like. The Pro Plus ballast 1025 is a compact electrical component, which interacts with the Pro Plus corona ozone generator 1032, the Pro Plus processor module 1026 and the Pro Plus power supply/UPS module 1039, and comprises a durable material, such as aluminum, metal, steel, composite material, or the like. The load weight sensor 1036 is a compact electrical component, which interacts with the Pro Plus processor module 1026, and comprises a durable material, such as aluminum, metal, steel, composite material, or the like. The plurality of Pro Plus perforated trays 1040 comprise a rigid perforated material, which allows free air flow through the Pro Plus perforated trays 1040, such as aluminum, metal, steel, plastic, composite material, wood, or the like. The Pro Plus outer vent 1014 comprise a rigid perforated material, which allows free air flow through the Pro Plus outer vent 1014, such as aluminum, metal, steel, plastic, composite material, wood, or the like. The Pro Plus casters 1034 comprise wheels and their supporting structure, and comprises rubber or plastic and a rigid durable material, such as aluminum, metal, steel, glass, plastic, polycarbonate, composite material, ceramic, fiberglass, wood, or the like. The materials listed herein are examples only and not intended to limit the scope of the present invention.

Figure 9:
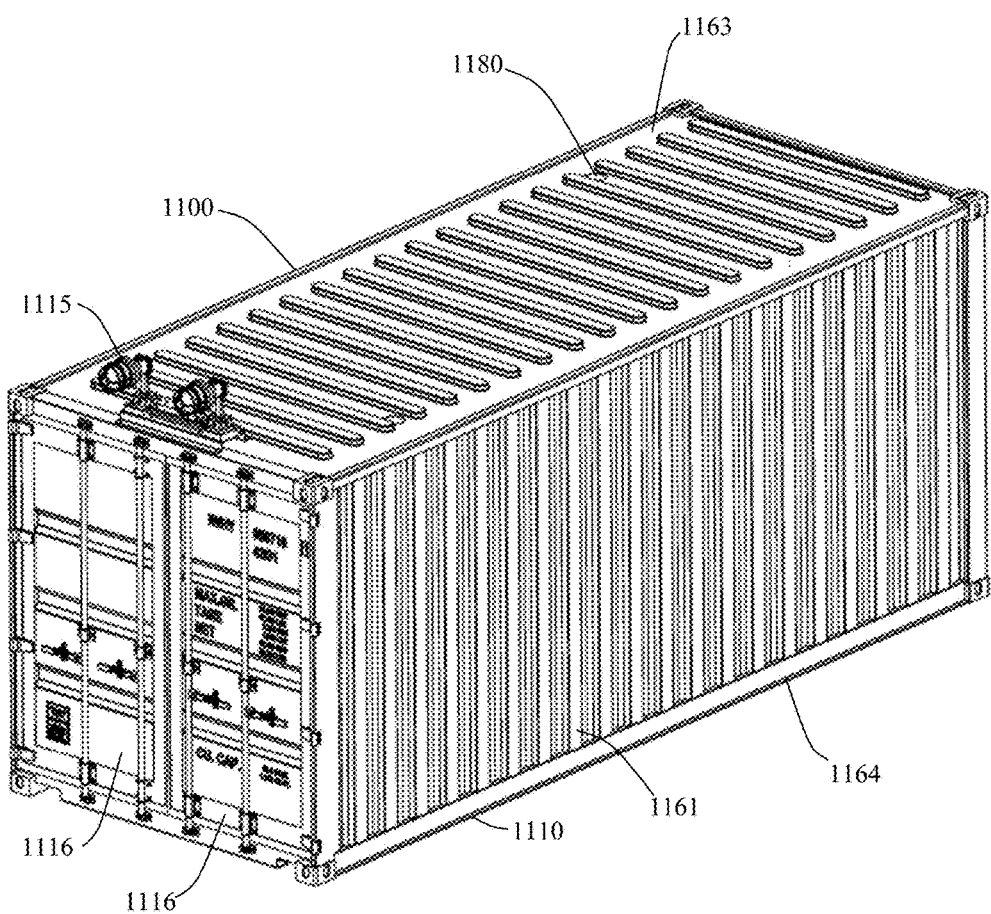
FIG. 9 is a perspective view of another preferred embodiment of an apparatus of the present invention.
Figure 10:
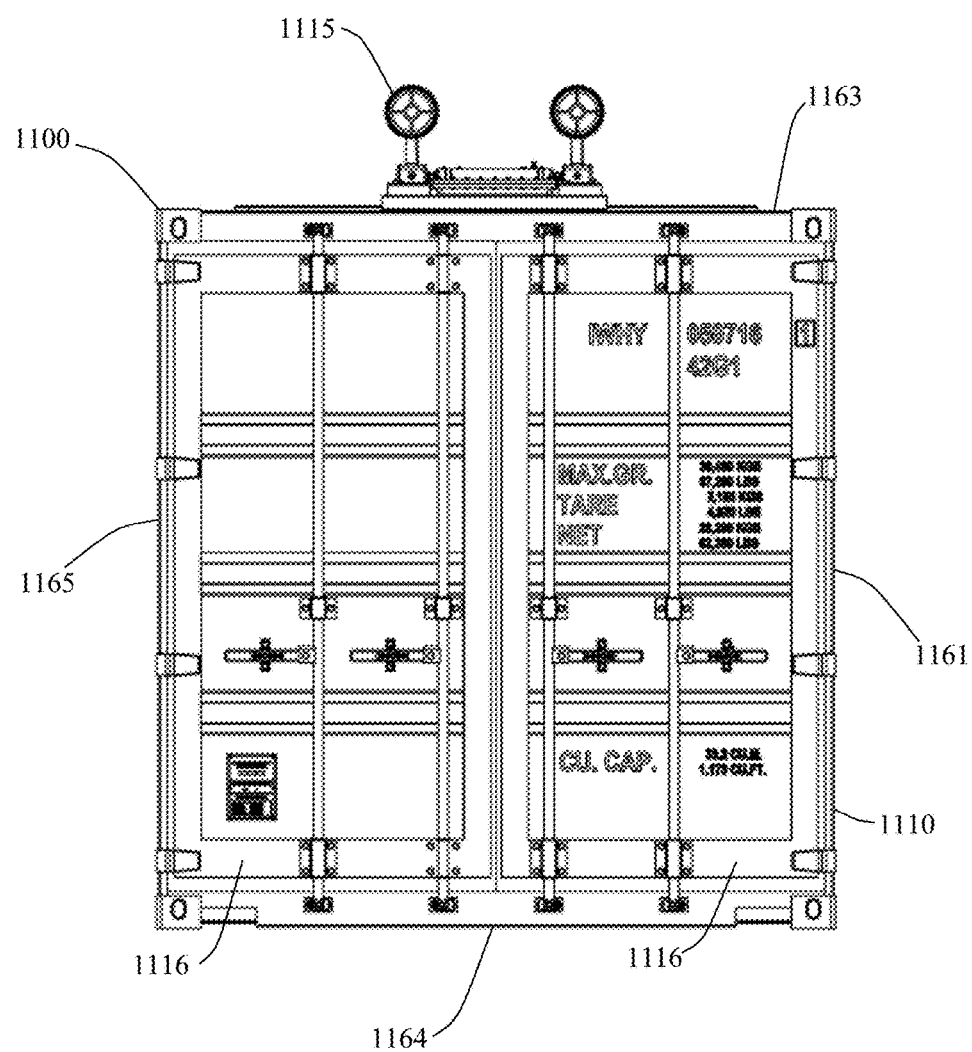
FIG. 10 is a front view of an apparatus of FIG. 9.
Figure 11:
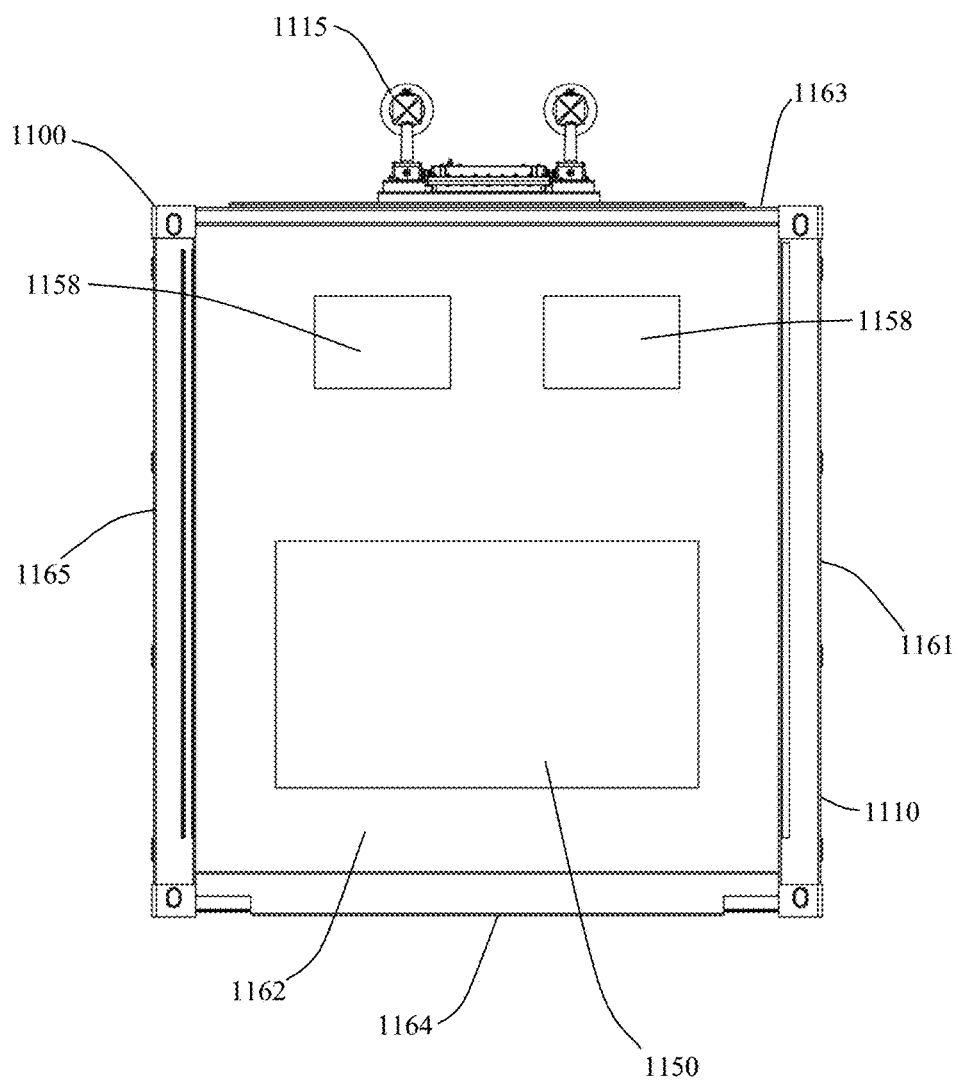
FIG. 11 is a rear view of an apparatus of FIG. 9.
Figure 12:
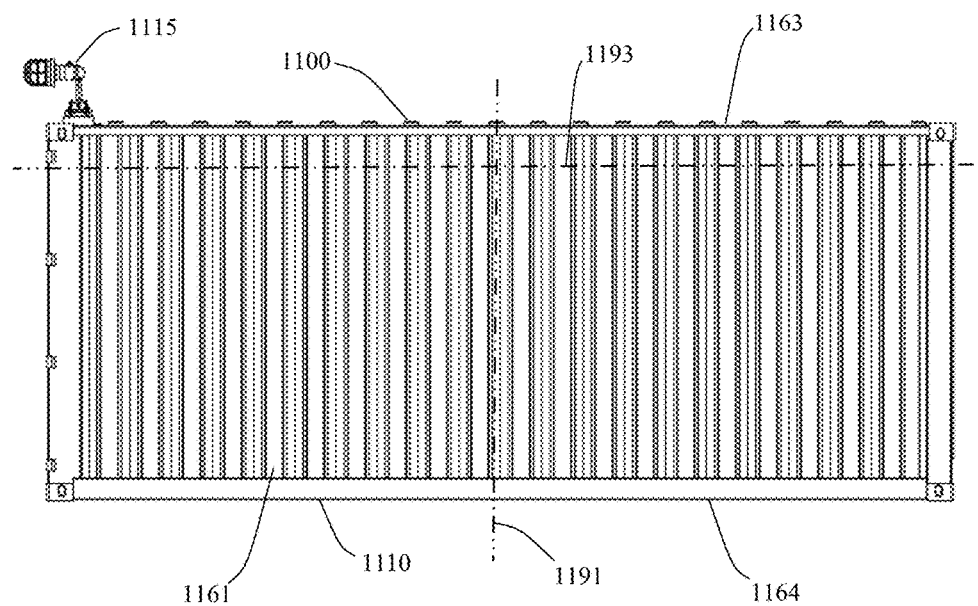
FIG. 12 is a right side view of an apparatus of FIG. 9.
Figure 13:
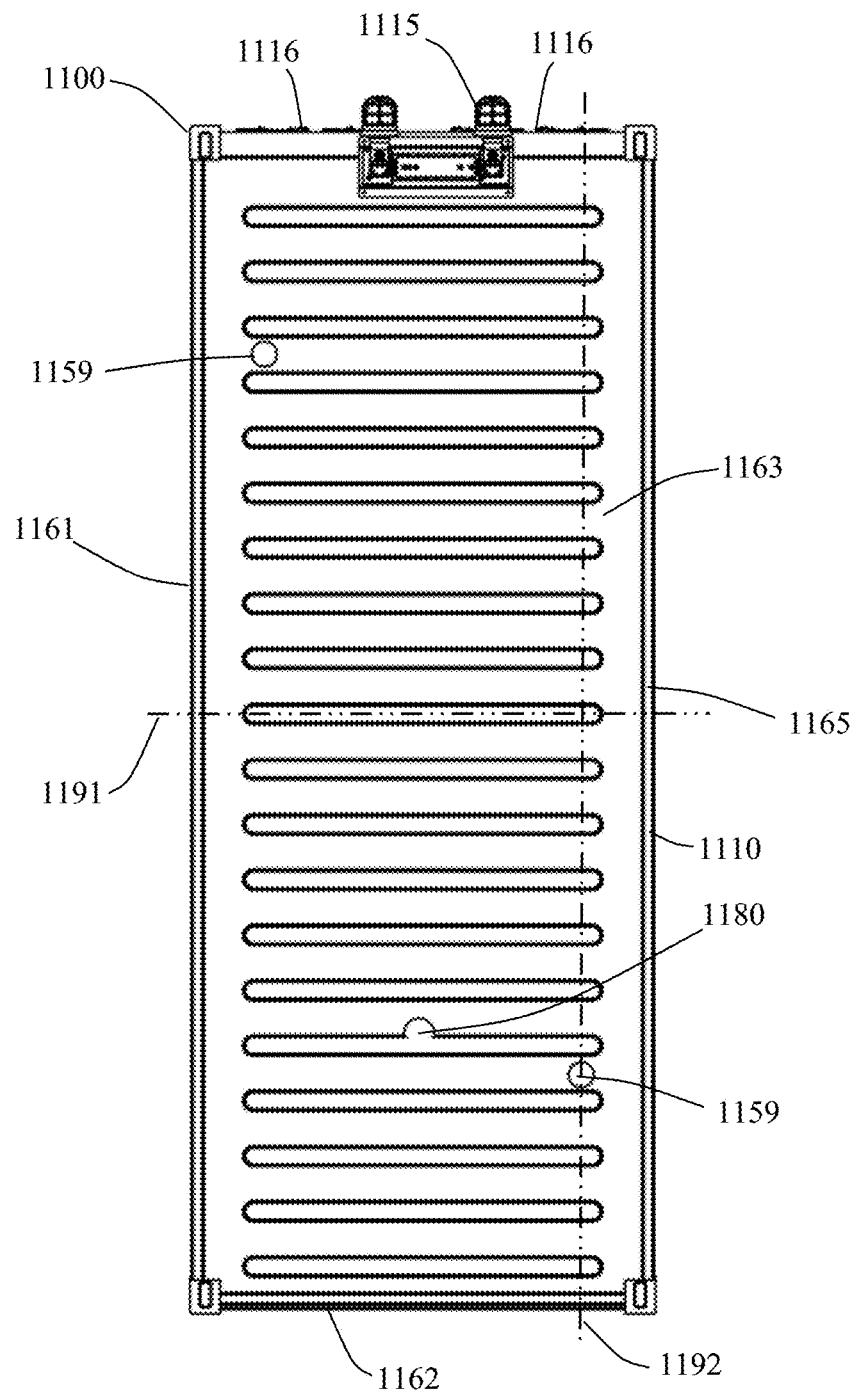
FIG. 13 is a top view of an apparatus of FIG. 9.
Figure 14:
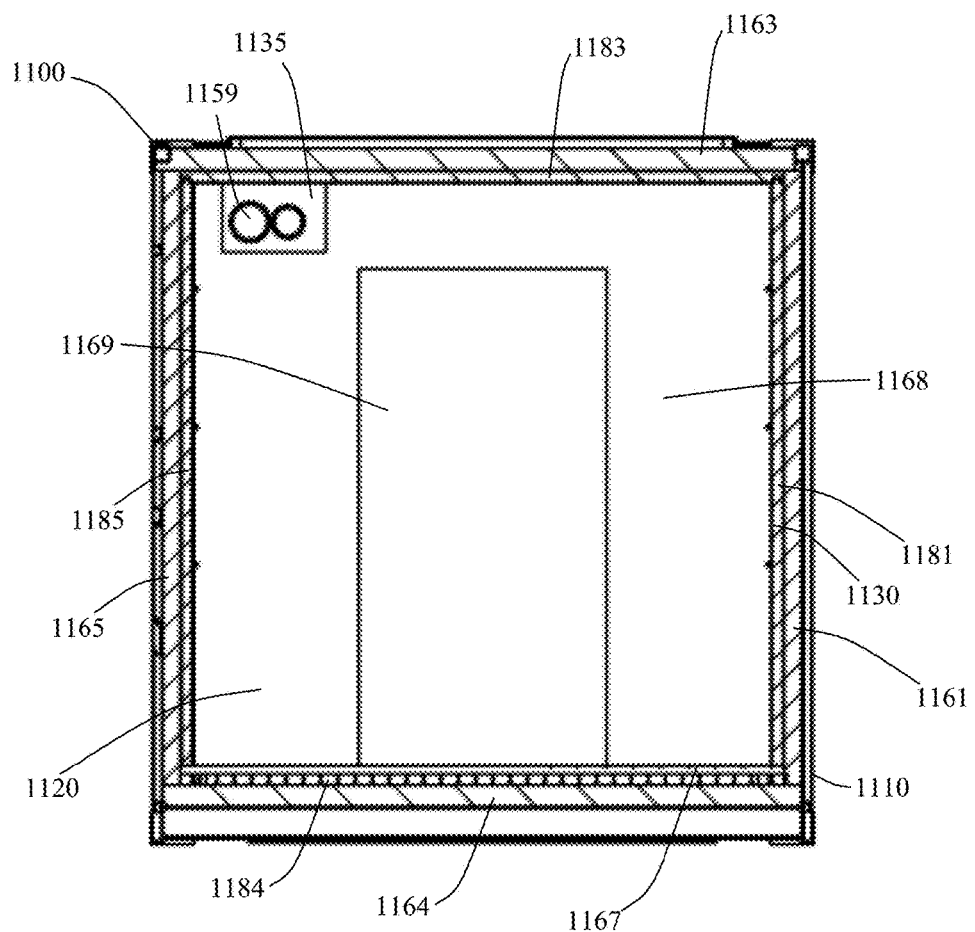
FIG. 14 is a front cutaway view of an apparatus of FIG. 9, showing the interior of the present invention.
Figure 15:
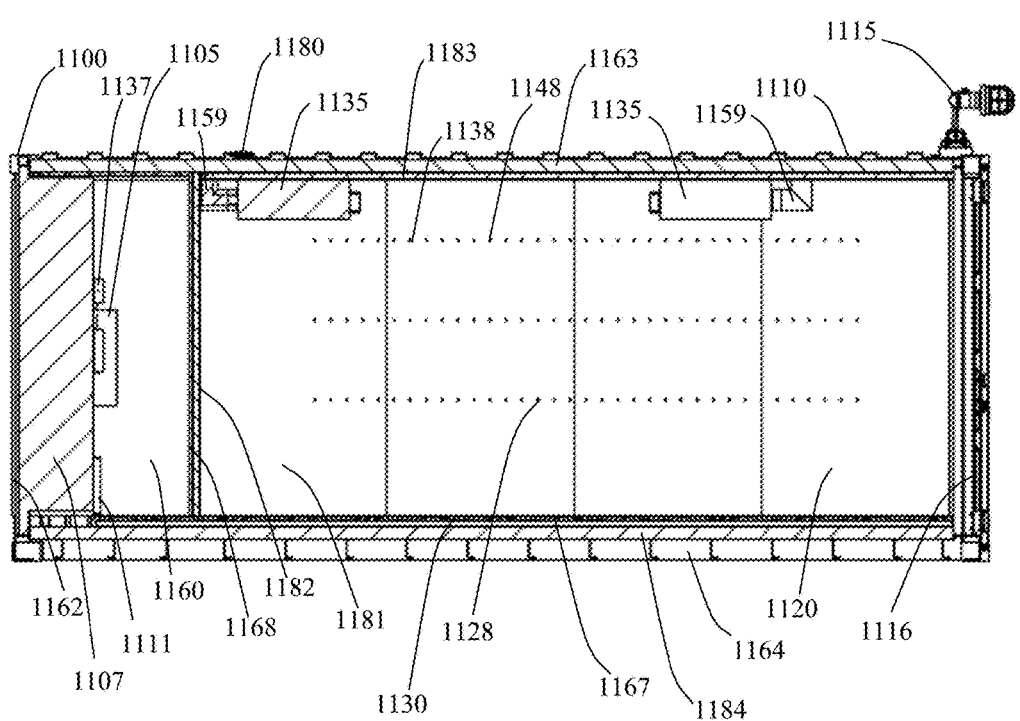
FIG. 15 is a left side cutaway view of an apparatus of FIG. 9, showing the interior of the present invention.
Figure 16:
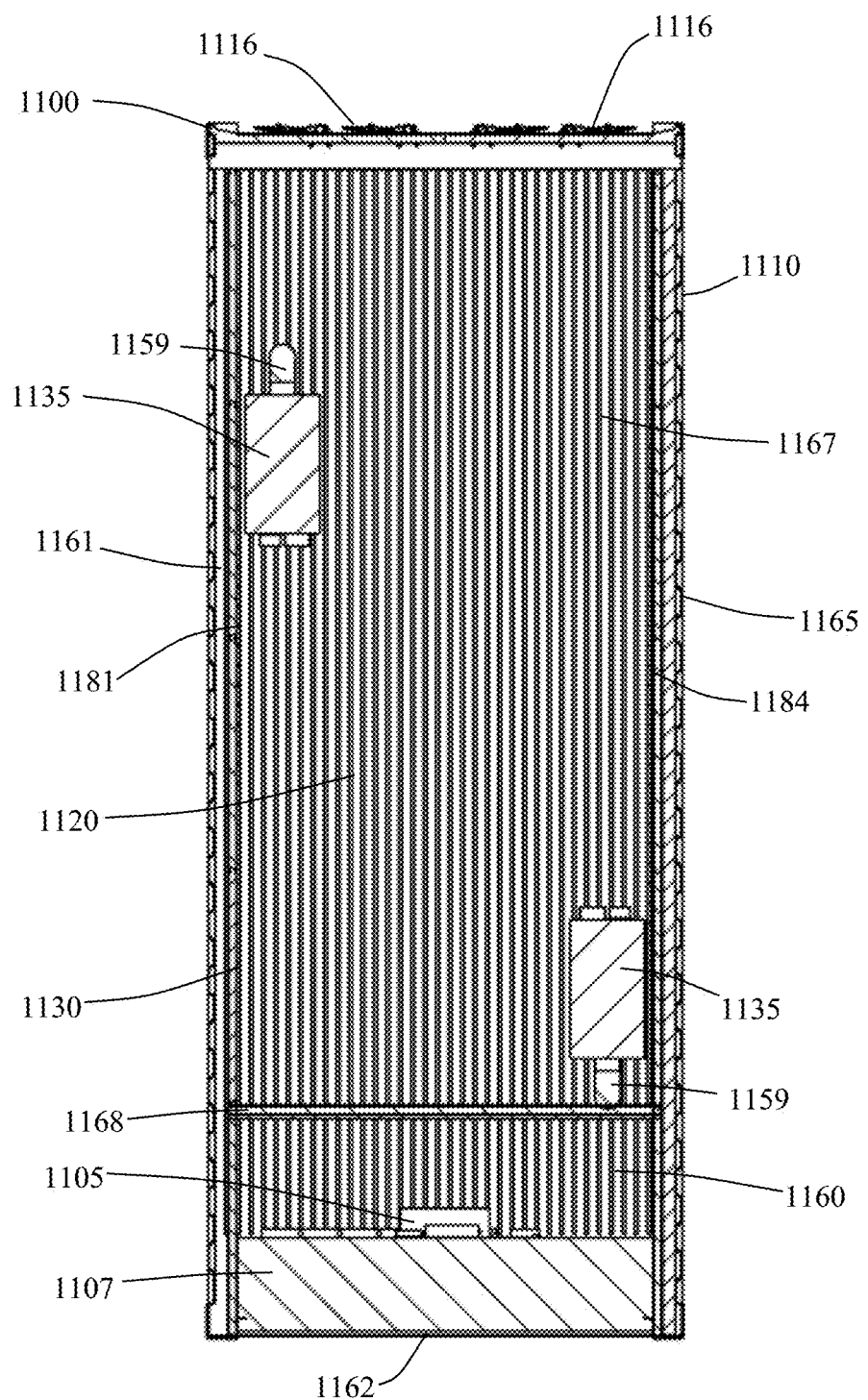
FIG. 16 is a top cutaway view of an apparatus of FIG. 9, showing the interior of the present invention.
Figure 17:
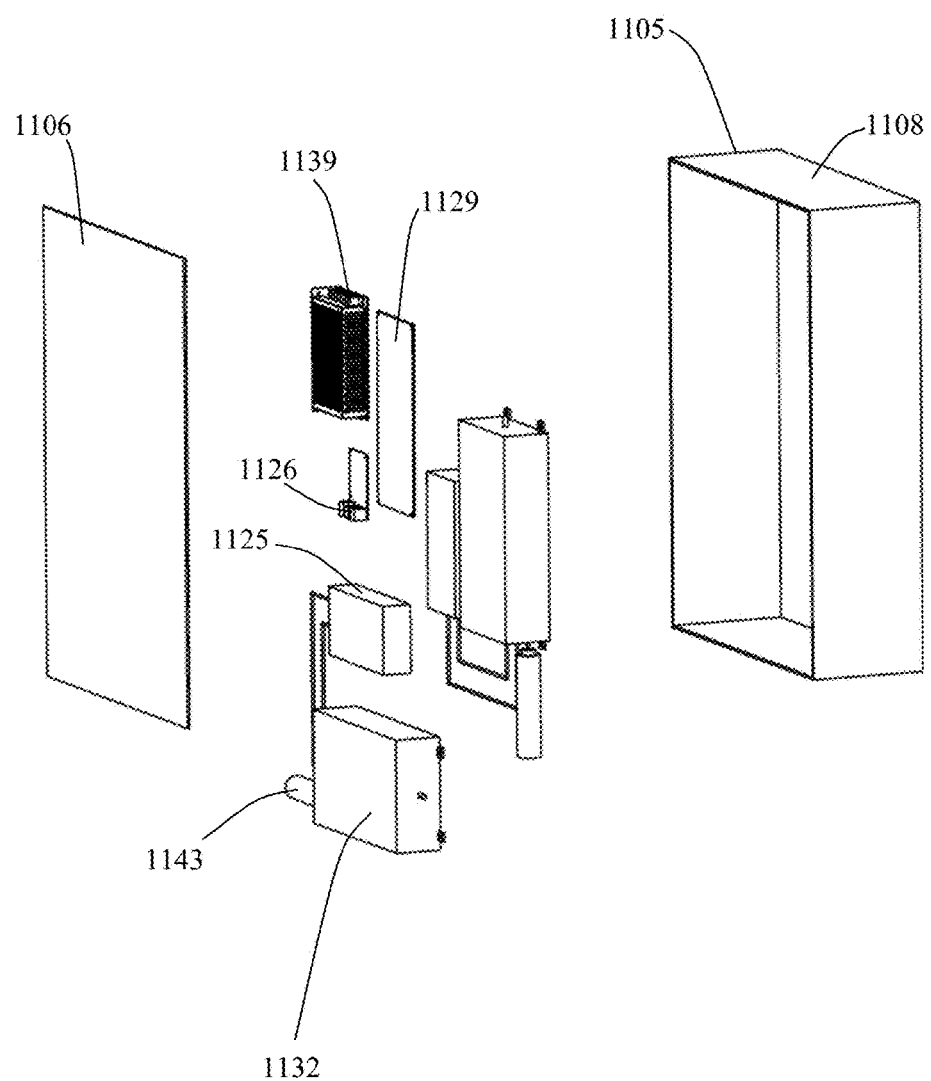
FIG. 17 is an exploded perspective view of the electronics cabinet an apparatus of FIG. 9.

Referring now to another more preferred embodiment of the present invention, in FIG. 9, FIG. 10 FIG. 11, FIG. 12, FIG. 13, FIG. 14, FIG. 15, FIG. 16, FIG. 17, FIG. 18, FIG. 19, FIG. 20, FIG. 21, FIG. 22, FIG. 23, and FIG. 24, a Refrigerated Neutral Atmosphere and Sanitization Storage Apparatus 1100 is shown. FIG. 9 illustrates a perspective view of a Refrigerated Neutral Atmosphere and Sanitization Storage Apparatus 1100. FIG. 10 depicts a front view of a Refrigerated Neutral Atmosphere and Sanitization Storage Apparatus 1100. FIG. 11 shows a rear view of a Refrigerated Neutral Atmosphere and Sanitization Storage Apparatus 1100. FIG. 12 displays a right side view of a Refrigerated Neutral Atmosphere and Sanitization Storage Apparatus 1100. FIG. 13 depicts a top view of a Refrigerated Neutral Atmosphere and Sanitization Storage Apparatus 1100. FIG. 14 illustrates a front cutaway view of a Refrigerated Neutral Atmosphere and Sanitization Storage Apparatus 1100 with the cutaway positioned at the dotted line 1191 in FIG. 12 and FIG. 13. FIG. 15 shows a left side cutaway view of a Refrigerated Neutral Atmosphere and Sanitization Storage Apparatus 1100 with the cutaway positioned at the dotted line 1192 in FIG. 13. FIG. 16 shows a top cutaway view of a Refrigerated Neutral Atmosphere and Sanitization Storage Apparatus 1100 with the cutaway positioned at the dotted line 1193 in FIG. 12. FIG. 17 demonstrates an exploded perspective view of a Refrigerated electronics cabinet 1105 of a Refrigerated Neutral Atmosphere and Sanitization Storage Apparatus 1100. FIG. 18 illustrates a cutaway view of a insulation panel 1175 used in a Refrigerated Neutral Atmosphere and Sanitization Storage Apparatus 1100 with the cutaway positioned at the dotted line 1194, showing the inner insulation 1178, the first outer veneer panel 1176 and second outer veneer panel 1177 of the insulated panel 1175. FIG. 19 displays a diagram, which describes the network configuration related to the Refrigerated Neutral Atmosphere and Sanitization Storage Apparatus 1100. FIG. 20 depicts a flow chart, which describes the process for setting up and configuring the Refrigerated Neutral Atmosphere and Sanitization Storage Apparatus 1100. FIG. 21 shows a flow chart, which describes the interactions of the web application 230, mobile application 240, network servers 210 and the Refrigerated Neutral Atmosphere and Sanitization Storage Apparatus 1100. FIG. 22 illustrates a flow chart, which describes the process for the manual operation of the Refrigerated Neutral Atmosphere and Sanitization Storage Apparatus 1100. FIG. 23 demonstrates a flow chart, which describes the process for the programmed operation of the Refrigerated Neutral Atmosphere and Sanitization Storage Apparatus 1100. FIG. 24 shows a diagram, which describes a most preferred embodiment of a network configuration related to the Refrigerated Neutral Atmosphere and Sanitization Storage Apparatus 1100.

Referring still to the more preferred embodiment of the invention, in FIG. 9, FIG. 10 FIG. 11, FIG. 12, FIG. 13, FIG. 14, FIG. 15, FIG. 16, FIG. 17, FIG. 18, FIG. 19, FIG. 20, FIG. 21, FIG. 22, FIG. 23, and FIG. 24, the Refrigerated Neutral Atmosphere and Sanitization Storage Apparatus 1100 comprises an openable and lockable Refrigerated outer shell assembly 1110, an insulated and airtight Refrigerated inner shell assembly 1130, and a Refrigerated exposure chamber 1120. The Refrigerated outer shell assembly 1110 comprises two Refrigerated insulated front doors 1116, a Refrigerated insulated left side panel 1165, a Refrigerated insulated right side panel 1161, a Refrigerated insulated rear panel 1162, a Refrigerated insulated top panel 1163, and a Refrigerated insulated bottom panel 1164. The improved insulation in the Refrigerated Neutral Atmosphere and Sanitization Storage Apparatus 1100 allows for improved precision with regards to temperature and humidity control. The two Refrigerated insulated front doors 1116 are lockable to prevent unauthorized access to the Refrigerated Neutral Atmosphere and Sanitization Storage Apparatus 1100 and are hingedly attached to the Refrigerated insulated left side panel 1165 and Refrigerated insulated right side panel 1161, respectively. The Refrigerated insulated left side panel 1165 is hingedly attached to a Refrigerated insulated front door 1116. The Refrigerated insulated right side panel 1161 is hingedly attached to a Refrigerated insulated front door 1116. The Refrigerated insulated rear panel 1162 comprises two Refrigerated rear outer vents 1158, which provides ventilation for the enclosed electronics and refrigerator unit 1107, and a Refrigerated insulated rear access door 1150. The Refrigerated insulated top panel 1163 comprises Refrigerated dehumidifier vents 1159, Refrigerated warning lights 1115 and a Refrigerated WiFi antenna 1180. The Refrigerated insulated bottom panel 1164 comprises a rigid base, which allows the Refrigerated Neutral Atmosphere and Sanitization Storage Apparatus 1100 to be fully transportable, such as by truck, train or ship. The Refrigerated insulated inner shell assembly 1130 is airtight when closed and comprises a Refrigerated floor grating 1167, a Refrigerated electronics chamber 1160 and a Refrigerated exposure chamber 1120. The Refrigerated electronics chamber 1160 and the Refrigerated exposure chamber 1120 are separated by a Refrigerated insulated back wall 1168, which comprises a Refrigerated insulated back wall door 1169. The Refrigerated electronics chamber 1160 comprises a Refrigerated electronics cabinet 1105, a Refrigerated radiant heater 1111, a Refrigerated fan 1137, and a refrigerator unit 1107. The Refrigerated electronics cabinet 1105 comprises a Refrigerated electronics cabinet base 1108, a Refrigerated electronics cabinet door 1106, a Refrigerated corona ozone generator 1132, a Refrigerated oxygen gas feed tank 1143, which may feed oxygen gas directly into the Refrigerated corona ozone generator 1132, a Refrigerated corona ozone generator ballast 1125, a Refrigerated Processor module 1126, a Refrigerator control board 1129, and a Refrigerated power supply/UPS module 1139. The refrigerator unit 1107 comprises an industrial refrigerator unit, which is capable of providing improved precision for temperature control as well as a wider range of temperature set points, including temperatures appropriate for refrigeration of any particular perishable items being stored within the apparatus and including, but not limited to, freezing temperatures. The Refrigerated exposure chamber cage 1120 is airtightably enclosed within the Refrigerated inner shell assembly 1130 and comprises a Refrigerated combined humidity and temperature sensor 1138, a Refrigerated ozone sensor 1148, Refrigerated precision dehumidifiers 1135 with Refrigerated dehumidifier vents 1159, Refrigerated hooks 1128 for receiving perforated trays, a Refrigerated insulated right side veneer 1181, a Refrigerated insulated rear veneer 1182, a Refrigerated insulated top veneer 1183, a Refrigerated insulated bottom veneer 1184, and a Refrigerated insulated left side veneer 1185. The veneer panels 1176, 1177, including the Refrigerated insulated right side veneer 1181, the Refrigerated insulated rear veneer 1182, the Refrigerated insulated top veneer 1183, the Refrigerated insulated bottom veneer 1184, and the Refrigerated insulated left side veneer 1185, comprise limestone, mahogany, a neutral composite material, or a like critical material, and provide the function of simulating the conditions of a cave for storing or aging cheese or, similarly, a wine cellar for storing wine while maintaining its quality. Further, the veneer panels 1176, 1177 may be incorporated into insulation panels 1175, which comprise inner insulation 1178, a first outer veneer panel 1176 and a second outer veneer panel 1177. Additionally, the Refrigerated insulated front doors 1116, Refrigerated insulated left side panel 1165, Refrigerated insulated right side panel 1161, Refrigerated insulated rear panel 1162, Refrigerated insulated top panel 1163, Refrigerated insulated bottom panel 1164, Refrigerated insulated rear access door 1150, Refrigerated insulated inner shell assembly 1130, Refrigerated insulated back wall 1168, and Refrigerated insulated back wall door 1169, may comprise insulation panels 1175. The refrigerator unit 1107 combined with the improved insulation provides improved precision for temperature control as well as a wider range of temperature set points, including temperatures appropriate for refrigeration of any particular perishable items being stored within the apparatus and including, but not limited to, freezing temperatures. The Refrigerated processor module 1126 is wirelessly networked through a direct Wi-Fi connection 720 or a direct Bluetooth connection 730 and capable of connecting to direct network servers 740 and, through the direct network servers 740, communicating with applications running on personal computers 770, smart phones 780 or tablets 790. Further, the Refrigerated processor module 1126 is capable of receiving information from the Refrigerated combined humidity and temperature sensor 1138 and Refrigerated ozone sensor 1148; directing the locking or unlocking of the Refrigerated front door 1116; controlling the Refrigerated warning lights 1115; and coordinating and dynamically controlling the Refrigerated corona ozone generator 1132, the Refrigerated oxygen gas feed tank 1143, the refrigerator unit 1107, the Refrigerated precision dehumidifier 1135 and the Refrigerated fan 1137. Because of the amount of power required to produce ozone and to facilitate the frequent operation of the present invention, the Refrigerated power supply/UPS module 1139 operates on standard 120 VAC and is also capable of providing uninterrupted power supply in case of a power outage or during transportation of the apparatus. The insulated Refrigerated inner shell assembly 1130 is openable using the Refrigerated insulated front doors 1116 and airtight when the Refrigerated insulated front doors 1116 are closed. The Refrigerated warning lights 1115 are controlled by the Refrigerated processor module 1126, and may be used to indicate whether the Refrigerated corona ozone generator 1132 is activated or other useful information about the present invention, such as temperature, humidity, and ozone readings or the contents of the perforated trays. The Refrigerated corona ozone generator 1132 is capable of converting ambient oxygen within the Refrigerated inner shell assembly 1130 into ozone (ozone saturation process), as well as supply additional ozone by converting oxygen from the Refrigerated oxygen gas feed tank 1143 into ozone, and is capable of being controlled by the Refrigerated processor module 1126. The Refrigerated Neutral Atmosphere and Sanitization Storage Apparatus 1100 may use perforated trays, which are sufficiently perforated to allow the free flow of air around any perishable item or biomass being stored within the apparatus. The Refrigerated combined humidity and temperature sensor 1138 is mounted in close proximity to the perforated trays and measures humidity and temperature levels within the Refrigerated inner shell assembly 1130 and relays the measured data to the Refrigerated processor module 1126, so that the data may be used to trigger certain actions by the Refrigerated processor module 1126, such as turning the Refrigerated corona ozone generator 1132 on or off, turning the refrigerator unit 1107 on or off, turning the Refrigerated precision dehumidifier 1135 on or off, turning the Refrigerated radiant heater 1111 on or off, sending one or more alerts, or the like. The Refrigerated ozone sensor 1148 is mounted in close proximity to the Refrigerated perforated trays 1140 and measures ozone levels within the Refrigerated inner shell assembly 1130 and relays the measured data to the Refrigerated processor module 1126, so that the data may be used to trigger certain actions by the Refrigerated processor module 1126, such as turning the Refrigerated corona ozone generator 1132 on or off turning the refrigerator unit 1107 on or off, turning the Refrigerated precision dehumidifier 1135 on or off, turning the Refrigerated radiant heater 1111 on or off, sending one or more alerts, or the like. The Refrigerated fan 1137 circulates the ambient air within the Refrigerated inner shell assembly 1130 in order to maximize its exposure to the Refrigerated corona ozone generator 1132 during the ozone saturation process. The perforated trays hold perishable items or biomass within the Refrigerated inner shell assembly 1130, so that the perishable items or biomass are sufficiently exposed to the air within the Refrigerated inner shell assembly 1130 to benefit from ozone saturation, temperature control, and humidity control, and stores the perishable items or biomass in a region that is readily accessible when the Refrigerated front door 1116 is open. The Refrigerated Neutral Atmosphere and Sanitization Storage Apparatus 1100 may be completely self-contained and, similar to a shipping container, fully transportable, such as by truck, train, or ship, and the technology can be retrofitted into existing standardized intermodal container designs.

The construction details of the invention as shown in FIG. 9, FIG. 10 FIG. 11, FIG. 12, FIG. 13, FIG. 14, FIG. 15, FIG. 16, FIG. 17, FIG. 18, FIG. 19, FIG. 20, FIG. 21, FIG. 22, FIG. 23, and FIG. 24, are as follows. The Refrigerated outer shell assembly 1110, including the Refrigerated insulated front doors 1116, the Refrigerated insulated left side panel 1165, the Refrigerated insulated right side panel 1161, the Refrigerated insulated rear access door 1150, the Refrigerated insulated rear panel 1162, the Refrigerated insulated top panel 1163, Refrigerated insulated back wall 1168, Refrigerated insulated back wall door 1169, and the Refrigerated insulated inner shell assembly 1130, comprise the inner insulation 1178, the first outer veneer panel 1176 and the second outer veneer panel 1177 of the insulated panel 1175 and may also comprise a strong, rigid, durable material, such as aluminum, metal, steel, glass, plastic, polycarbonate, composite material, ceramic, fiberglass, other types of wood, or the like. The veneer panels 1176, 1177 comprise limestone, mahogany, a neutral composite material, or a like critical material, and provide the function of simulating the conditions of a cave for storing or aging cheese or, similarly, a wine cellar for storing wine while maintaining its quality. The inner insulation 1178 comprises composite insulation, cotton, foam, plastic, ceramic, fiberglass, wood, or the like. The Refrigerated power supply/UPS module 1139 comprises a transformer, a 120 VAC power source, an electronic ballast, a battery pack, a uninterrupted power supply (UPS), a solar cell, or the like, and may allow for the apparatus to be self-contained. The Refrigerated processor module 1126 comprises a compact wirelessly connected computer. The Refrigerated corona ozone generator 1132 comprises a device that generates an electric field in the presence of oxygen, as well as, the electrical connections for the generator. The Refrigerated oxygen gas feed tank 1143 is capable of holding pressurized oxygen gas and feeding the oxygen gas directly to the Refrigerated corona ozone generator 1132 and comprises a strong, rigid, durable material that is resistant to pure oxygen gas, such as metal, steel, glass, composite material, ceramic, or the like. The Refrigerated fan 1137 is a compact electrical component, which interacts with the Refrigerated processor module 1126 and the Refrigerated power supply/UPS module 1139, and comprises a durable material, such as aluminum, metal, steel, plastic, composite material, or the like. The Refrigerated combined humidity and temperature sensor 1138 is a compact electrical component, which interacts with the Refrigerated processor module 1126, and comprises a durable material, such as aluminum, metal, steel, plastic, composite material, or the like. The Refrigerated ozone sensor 1138 is a compact electrical component, which interacts with the Refrigerated processor module 1126, and comprises a durable material, such as aluminum, metal, steel, plastic, composite material, or the like. The Refrigerated precision dehumidifier 1135 is a compact electrical component, which interacts with the Refrigerated processor module 1126 and the Refrigerated power supply/UPS module 1139, and comprises a durable material, such as aluminum, metal, steel, plastic, composite material, or the like. The refrigerator unit 1107 is a compact electrical component, which provides cooling by removing heat, which interacts with the Refrigerated processor module 1126 and the Refrigerated power supply/UPS module 1139, and comprises a durable material, such as aluminum, metal, steel, plastic, composite material, or the like. The Refrigerated warning lights 1115 are compact electrical components, which interacts with the Refrigerated processor module 1126 and the Refrigerated power supply/UPS module 1139, and comprises a durable material, such as aluminum, metal, steel, glass, plastic, composite material, or the like. The Refrigerated ballast 1125 is a compact electrical component, which interacts with the Refrigerated corona ozone generator 1132, the Refrigerated processor module 1126 and the Refrigerated power supply/UPS module 1139, and comprises a durable material, such as aluminum, metal, steel, composite material, or the like. The Refrigerated radiant heater 1111 is a compact electrical component, which generated heat, which interacts with the Refrigerated processor module 1126, and comprises a durable material, such as aluminum, metal, steel, composite material, or the like. The perforated trays comprise a rigid perforated material, which allows free air flow through the perforated trays, such as aluminum, metal, steel, plastic, composite material, wood, or the like. The Refrigerated dehumidifier vent 1159 comprise a rigid perforated material, which allows free air flow through the Refrigerated dehumidifier vent 1159, such as aluminum, metal, steel, plastic, composite material, wood, or the like. The Refrigerated rear outer vents 1158 comprise a rigid perforated material, which allows free air flow through the Refrigerated rear outer vents 1158, such as aluminum, metal, steel, plastic, composite material, wood, or the like. The materials listed herein are examples only and not intended to limit the scope of the present invention.

Referring now to the invention of FIG. 1, FIG. 2, FIG. 3, FIG. 4, FIG. 5, FIG. 6, FIG. 7, FIG. 8, FIG. 9, FIG. 10, FIG. 11, FIG. 12, FIG. 13, FIG. 14, FIG. 15, FIG. 16, FIG. 17, FIG. 18, FIG. 19, FIG. 20, FIG. 21, FIG. 22, FIG. 23, and FIG. 24, in further detail, FIG. 19 depicts a diagram, which describes a preferred embodiment of a network configuration related to the Pro Plus Neutral Atmosphere and Sanitization Storage Apparatus 1000 and the Refrigerated Neutral Atmosphere and Sanitization Storage Apparatus 1100. The Pro Plus Neutral Atmosphere and Sanitization Storage Apparatus 1001 and the Refrigerated Neutral Atmosphere and Sanitization Storage Apparatus 1100, may be controlled through a web application 230 using a desktop computer or a mobile application 240 using a smartphone or tablet. Each Pro Plus Neutral Atmosphere and Sanitization Storage Apparatus 1000 and Refrigerated Neutral Atmosphere and Sanitization Storage Apparatus 1100, may connect to network servers 210 through a firewall 220 using a Wi-Fi connection 260. Each running web application 230 connects to network servers 210 through a firewall 220 using an application network connection 250. The application network connection 250 comprises a wired network connection, a wireless connection, and/or a cellular connection. Similarly, each running mobile application 240 connects to network servers 210 through a firewall 220 using an application network connection 250. This network structure allows a Pro Plus Neutral Atmosphere and Sanitization Storage Apparatus 1000 or Refrigerated Neutral Atmosphere and Sanitization Storage Apparatus 1100, in one location to be remotely controlled and/or monitored from any other location where an application network connection 250 can be established to access the network servers 210. After a user initially connects the system and enables network communications, the wirelessly networked processor module 126 automatically seeks out a Wi-Fi network and connects with network servers 210 using a Wi-Fi connection 260. The user then creates login information, registers the Pro Plus Neutral Atmosphere and Sanitization Storage Apparatus 1000 or the Refrigerated Neutral Atmosphere and Sanitization Storage Apparatus 1100, and sets preferences and alert settings for the apparatus. Network servers 210 record settings and begins to monitor the system and maintain diagnostic records on all tracked elements, including, but not limited to, relative humidity, ozone levels, ozone generation cycles, temperature, access (opening/closing) of the system, or the like. The Pro Plus Neutral Atmosphere and Sanitization Storage Apparatus 1000 or the Refrigerated Neutral Atmosphere and Sanitization Storage Apparatus 1100 provide a cloud-based monitoring system for all diagnostics and alerts generated for all deployed systems. Using a web application 230 on a desktop computer or a mobile application 240 on a smart phone (iOS or android), a user may monitor and/or control various aspects of the Pro Plus Neutral Atmosphere and Sanitization Storage Apparatus 1000 or the Refrigerated Neutral Atmosphere and Sanitization Storage Apparatus 1100, including, but not limited to, opening and closing the lids or doors, locking and unlocking the apparatuses, initiating preprogramed treatment cycles, programming the decay periods between openings, monitoring the temperature and relative humidity (RH) within the insulated airtight enclosures, monitoring the ozone levels within the insulated airtight enclosures, recording the type of perishable items being stored, displaying or editing a user profile, accessing blogs or FAQs concerning recommendations for storing different types of perishable items, time, setting alerts, displaying the serial number or other identifying information of the apparatus, triggering a hard reset, activating off grid settings, or other custom attributes.

Referring still to the invention of FIG. 1, FIG. 2, FIG. 3, FIG. 4, FIG. 5, FIG. 6, FIG. 7, FIG. 8, FIG. 9, FIG. 10, FIG. 11, FIG. 12, FIG. 13, FIG. 14, FIG. 15, FIG. 16, FIG. 17, FIG. 18, FIG. 19, FIG. 20, FIG. 21, FIG. 22, FIG. 23, and FIG. 24, in further detail, FIG. 24 depicts a diagram, which describes the most preferred embodiment of a network configuration related to the use of a single apparatus 700, such as a Pro Plus Neutral Atmosphere and Sanitization Storage Apparatus 1000 or a Refrigerated Neutral Atmosphere and Sanitization Storage Apparatus 1100, or of multiple apparatuses 710, including a collection of Pro Plus Neutral Atmosphere and Sanitization Storage Apparatuses 1000 or Refrigerated Neutral Atmosphere and Sanitization Storage Apparatuses 1100. The Pro Plus Neutral Atmosphere and Sanitization Storage Apparatus 1000 or the Refrigerated Neutral Atmosphere and Sanitization Storage Apparatus 1100 are primarily controlled through an application running on personal computers 770, smart phones 780 or tablets 790. Each Pro Plus Neutral Atmosphere and Sanitization Storage Apparatus 1000 or Refrigerated Neutral Atmosphere and Sanitization Storage Apparatus 1100, uses a direct Wi-Fi connection 720 or direct Bluetooth connection 730 to connect directly to direct network servers 740. Encryption keys are stored within each unit for security. Each application running on personal computers 770, smart phones 780 or tablets 790, directly connects to direct network servers 740, as well. This network structure allows a Pro Plus Neutral Atmosphere and Sanitization Storage Apparatus 1000 or Refrigerated Neutral Atmosphere and Sanitization Storage Apparatus 1100, in one location to be remotely controlled and/or monitored from any other location where a direct network connection to a direct network server 740 may be established by a personal computer 770, smart phone 780 or tablet 790. After a user initially connects the system and enables network communications, the wirelessly networked Pro Plus processor module 1026 or the Refrigerated processor module 1126 automatically seeks out a Wi-Fi network and connects with direct network servers 740 using a direct Wi-Fi connection 720 or a direct Bluetooth connection 730. The user then creates login information, registers the apparatus, and sets preferences and alert settings for the apparatus. Direct Network servers 740 record settings and begins to monitor the system and maintain diagnostic records on all tracked elements, including, but not limited to, relative humidity, ozone levels, ozone generation cycles, temperature, weight, access (opening/closing) of the system, or the like. The Pro Plus Neutral Atmosphere and Sanitization Storage Apparatus 1000 or the Refrigerated Neutral Atmosphere and Sanitization Storage Apparatus 1100, provide cloud-based monitoring systems for all diagnostics and alerts generated for all deployed systems. Using an application on a personal computer 770, smart phone 780 or tablet 790, a user may monitor and/or control various aspects of the Pro Plus Neutral Atmosphere and Sanitization Storage Apparatus 1000 or the Refrigerated Neutral Atmosphere and Sanitization Storage Apparatus 1100, including, but not limited to, opening and closing the lid or door, locking and unlocking the apparatuses, initiating preprogramed treatment cycles, programming the decay periods between openings, monitoring the temperature and relative humidity (RH) within the insulated airtight enclosures, monitoring the ozone level within the insulated airtight enclosures, recording the type of perishable items or biomass being stored, recording and logging the weight of the perishable items or biomass displaying or editing a user profile, accessing blogs or FAQs concerning recommendations for storing different types of perishable items, time, setting alerts, displaying the serial number or other identifying information of the apparatuses, triggering a hard resets, activating off grid settings, or other custom attributes.

Referring still to the invention of FIG. 1, FIG. 2, FIG. 3, FIG. 4, FIG. 5, FIG. 6, FIG. 7, FIG. 8, FIG. 9, FIG. 10, FIG. 11, FIG. 12, FIG. 13, FIG. 14, FIG. 15, FIG. 16, FIG. 17, FIG. 18, FIG. 19, FIG. 20, FIG. 21, FIG. 22, FIG. 23, and FIG. 24, in further detail, FIG. 20 depicts the initial configuration flow chart 300, which describes the process for setting up and configuring the Pro Plus Neutral Atmosphere and Sanitization Storage Apparatus 1000 or the Refrigerated Neutral Atmosphere and Sanitization Storage Apparatus 1100. First, in the activation step 310, the user activates the Pro Plus Neutral Atmosphere and Sanitization Storage Apparatus 1000 or the Refrigerated Neutral Atmosphere and Sanitization Storage Apparatus 1100, either by using a web application 230 or mobile application 240, or an application running on a personal computer 770, smart phone 780 or tablet 790, or, in some embodiments, a manual switch on the apparatus. Next, in the network connection step 320, the user connects the Pro Plus Neutral Atmosphere and Sanitization Storage Apparatus 1000 or the Refrigerated Neutral Atmosphere and Sanitization Storage Apparatus 1100, to network servers 210 using a web application 230 or mobile application 240, or through a direct Wi-Fi connection 720 or a direct Bluetooth connection 730 to a direct network server 740. Next, in the registration step 330, the user registers the Pro Plus Neutral Atmosphere and Sanitization Storage Apparatus 1000 or the Refrigerated Neutral Atmosphere and Sanitization Storage Apparatus 1100, on the network servers 210 using a web application 230 or mobile application 240, or an application running on a personal computer 770, smart phone 780 or tablet 790, through a direct Wi-Fi connection 720 or a direct Bluetooth connection 730 to a direct network server 740. Next, in the settings decision step 340, the user decides whether to use the default settings of the Pro Plus Neutral Atmosphere and Sanitization Storage Apparatus 1000 or the Refrigerated Neutral Atmosphere and Sanitization Storage Apparatus 1100, or to change them. If the user decides to use the default settings, the web application 230 or mobile application 240; or an application running on a personal computer 770, smart phone 780 or tablet 790 through a direct Wi-Fi connection 720 or a direct Bluetooth connection 730 to a direct network server 740; loads the default settings into the Pro Plus Neutral Atmosphere and Sanitization Storage Apparatus 1000 or the Refrigerated Neutral Atmosphere and Sanitization Storage Apparatus 1100; and the apparatus begins to track alerts for variations from the default settings, in the load system step 360. If the user decides to change the settings and use a configuration different from the default settings, the user accesses the web application 230 or mobile application 240; or an application running on a personal computer 770, smart phone 780 or tablet 790 through a direct Wi-Fi connection 720 or a direct Bluetooth connection 730 to a direct network server 740; and configures the settings to the desired monitoring levels, in the configure setting step 350. The Pro Plus Neutral Atmosphere and Sanitization Storage Apparatus 1000 or the Refrigerated Neutral Atmosphere and Sanitization Storage Apparatus 1100, can monitor parameters and send alerts to the web application 230 or mobile application 240; or an application running on a personal computer 770, smart phone 780 or tablet 790 through a direct Wi-Fi connection 720 or a direct Bluetooth connection 730 to a direct network server 740; when a parameter substantially varies from its setting. The adjustable tracking and monitoring parameters comprise whether and when Pro Plus Neutral Atmosphere and Sanitization Storage Apparatus 1000 or the Refrigerated Neutral Atmosphere and Sanitization Storage Apparatus 1100, is opened or closed, the number and frequency of ozone saturation process cycles, decay cycles, temperature levels, ozone levels, weights, relative humidity (RH) levels, type of perishable item being stored, user profile, the timing of events on the apparatuses, number of hard recycle orders, and information relevant to off grid operation. After the custom settings are configured, the web application 230 or mobile application 240; or an application running on a personal computer 770, smart phone 780 or tablet 790 through a direct Wi-Fi connection 720 or a direct Bluetooth connection 730 to a direct network server 740; loads the custom settings into the Pro Plus Neutral Atmosphere and Sanitization Storage Apparatus 1000 or the Refrigerated Neutral Atmosphere and Sanitization Storage Apparatus 1100, and apparatus begins to track alerts for variations from the custom settings, in the load system step 360. Once the load system step 360 is performed, the Pro Plus Neutral Atmosphere and Sanitization Storage Apparatus 1000 or the Refrigerated Neutral Atmosphere and Sanitization Storage Apparatus 1100, continues to monitor parameters for substantial variations from the recorded settings and sends alerts to the web application 230 or mobile application 240; or an application running on a personal computer 770, smart phone 780 or tablet 790 through a direct Wi-Fi connection 720 or a direct Bluetooth connection 730 to a direct network server 740; when a substantial variation occurs.

Referring still to the invention of FIG. 1, FIG. 2, FIG. 3, FIG. 4, FIG. 5, FIG. 6, FIG. 7, FIG. 8, FIG. 9, FIG. 10, FIG. 11, FIG. 12, FIG. 13, FIG. 14, FIG. 15, FIG. 16, FIG. 17, FIG. 18, FIG. 19, FIG. 20, FIG. 21, FIG. 22, FIG. 23, and FIG. 24, in further detail, FIG. 21 shows the application/network control flow chart 400, which describes the interactions of the web application 230, mobile application 240, network servers 210; or an application running on a personal computer 770, smart phone 780 or tablet 790 through a direct Wi-Fi connection 720 or a direct Bluetooth connection 730 to a direct network server 740; and the Pro Plus Neutral Atmosphere and Sanitization Storage Apparatus 1000 or the Refrigerated Neutral Atmosphere and Sanitization Storage Apparatus 1100. First, in the network ping step 410, the network servers 210 or direct network server 740 ping the Pro Plus Neutral Atmosphere and Sanitization Storage Apparatus 1000 or the Refrigerated Neutral Atmosphere and Sanitization Storage Apparatus 1100 through a firewall 220 using the wireless connection 260; or through a direct Wi-Fi connection 720 or a direct Bluetooth connection 730 to a direct network server 740. Next, in the box response step 420, the Pro Plus Neutral Atmosphere and Sanitization Storage Apparatus 1000 or the Refrigerated Neutral Atmosphere and Sanitization Storage Apparatus 1100 responds to the network servers 210 or direct network server 740, and provides updated values for all of the parameters that are being tracked to the network servers 210 or direct network servers 740. These tracked parameters comprise data regarding the opening and closing the lid, information relevant to locking and unlocking the apparatus, time and type of ozone saturation process or treatment cycles, decay periods between openings of the apparatus, temperature and relative humidity (RH) within the insulated airtight enclosure, ozone levels within the insulated airtight enclosure, the type of perishable items or biomass being stored, weight of perishable items or biomass being stored, user profile information, time data, alert settings, the serial number or other identifying information of the apparatus, or other custom parameters. Once the Pro Plus Neutral Atmosphere and Sanitization Storage Apparatus 1000 or the Refrigerated Neutral Atmosphere and Sanitization Storage Apparatus 1100, has updated the network servers 210 or direct network server 740 with current tracking data, a user may access and view performance data using the web application 230 or the mobile application 240; or an application running on a personal computer 770, smart phone 780 or tablet 790 through a direct Wi-Fi connection 720 or a direct Bluetooth connection 730 to a direct network server 740; in the available data step 430. If the parameters that are updated to the network servers 210 or direct network servers 740 from the Pro Plus Neutral Atmosphere and Sanitization Storage Apparatus 1000 or the Refrigerated Neutral Atmosphere and Sanitization Storage Apparatus 1100 fall outside the settings that are saved on the network servers 210 or the direct network servers 740, the network servers 210 or direct network servers 740 generate an alert in the alert generation step 450, which is displayed on the web application 230 or the mobile application 240 or on an application running on a personal computer 770, smart phone 780 or tablet 790 connected to a direct network server 740 through a direct Wi-Fi connection 720 or a direct Bluetooth connection 730. Next, in the change decision step 460, a decision is made as to whether a change is required in response to a generated alert. If an alert requires a change to the system, in the adjustment step 440, adjustments to the setting or controls are sent from the web application 230 or mobile application 240, or an application running on a personal computer 770, smart phone 780 or tablet 790, to the network servers 210 or direct network server 740 through a direct Wi-Fi connection 720 or a direct Bluetooth connection 730; and then to the Pro Plus Neutral Atmosphere and Sanitization Storage Apparatus 1000 or the Refrigerated Neutral Atmosphere and Sanitization Storage Apparatus 1100. If the apparatus receive a control adjustment directive, the appropriate elements of the Pro Plus Neutral Atmosphere and Sanitization Storage Apparatus 1000 or the Refrigerated Neutral Atmosphere and Sanitization Storage Apparatus 1100 are activated in order to manifest the desired change. For example, if an alert indicates that an ozone saturation process is recommended, the Pro Plus Neutral Atmosphere and Sanitization Storage Apparatus 1000 or the Refrigerated Neutral Atmosphere and Sanitization Storage Apparatus 1100 receives a signal to activate an ozone saturation process as defined in the settings on the network servers 210. In the green metrics step 470, once the tracked parameters of the Pro Plus Neutral Atmosphere and Sanitization Storage Apparatus 1000 or the Refrigerated Neutral Atmosphere and Sanitization Storage Apparatus 1100 fall within settings on the network servers 210 or direct network server 740, any alerts are cleared, and no further action is required.

Referring still to the invention of FIG. 1, FIG. 2, FIG. 3, FIG. 4, FIG. 5, FIG. 6, FIG. 7, FIG. 8, FIG. 9, FIG. 10, FIG. 11, FIG. 12, FIG. 13, FIG. 14, FIG. 15, FIG. 16, FIG. 17, FIG. 18, FIG. 19, FIG. 20, FIG. 21, FIG. 22, FIG. 23, and FIG. 24, in further detail, FIG. 22 illustrates the manual operation flow chart 500, which describes the process for the manual operation of the Pro Plus Neutral Atmosphere and Sanitization Storage Apparatus 1000 or the Refrigerated Neutral Atmosphere and Sanitization Storage Apparatus 1100. First, in the new product step 510, a user opens the Pro Plus Neutral Atmosphere and Sanitization Storage Apparatus 1000 or the Refrigerated Neutral Atmosphere and Sanitization Storage Apparatus 1100 and places fresh perishable items or biomass into apparatus for treatment and storage and then closes the apparatus. Next, in the activate hard cycle step 520, using a web application 230 or mobile application 240; or an application running on a personal computer 770, smart phone 780 or tablet 790 through a direct Wi-Fi connection 720 or a direct Bluetooth connection 730; a user connects to network servers 210 or direct network server 740 and activates a user mandated hard cycle. Next, in the hard cycle confirmation step 530, the network servers 210, or direct network servers 740, receives the user mandated hard cycle request and alerts the user to the request, and, after the user confirms the request using the web application 230 or mobile application 240; or an application running on a personal computer 770, smart phone 780 or tablet 790 through a direct Wi-Fi connection 720 or a direct Bluetooth connection 730 to a direct network server 740; the network servers 210 or direct network server 740 activate the ozone saturation process on the Pro Plus Neutral Atmosphere and Sanitization Storage Apparatus 1000 or the Refrigerated Neutral Atmosphere and Sanitization Storage Apparatus 1100. In the manual ozone saturation process step 540, in response to instructions from the network servers 210 or direct network servers 740, the Pro Plus Neutral Atmosphere and Sanitization Storage Apparatus 1000 or the Refrigerated Neutral Atmosphere and Sanitization Storage Apparatus 1100 activates the ozone saturation process. The ozone saturation process comprises turning on a corona ozone generator with an oxygen gas feed and a fan for an amount of time; which are precisely calculated based on the volume of the apparatus, the temperature and humidity inside the insulated airtight enclosure, the ozone level measured within the insulated airtight enclosure, the type and/or weight of the perishable items being sanitized, or the like, and keyed to proprietary tables; or which are determined by custom settings. Too little ozone saturation will not properly sanitize the perishable items or biomass, and too much ozone saturation may damage the perishable items or biomass. Next, in the rest cycle step 550, the ozone saturation process completes, and the rest cycle for the Pro Plus Neutral Atmosphere and Sanitization Storage Apparatus 1000 or the Refrigerated Neutral Atmosphere and Sanitization Storage Apparatus 1100 commences. Next, in the new batch decision step 560, the user determines whether a new batch of fresh perishable items or biomass is available. If a new batch of fresh perishable items or biomass is available, the user begins the new product step 510. If a new batch of fresh perishable items is not available, the manual operation process is completed in the stop step 570.

Referring still to the invention of FIG. 1, FIG. 2, FIG. 3, FIG. 4, FIG. 5, FIG. 6, FIG. 7, FIG. 8, FIG. 9, FIG. 10, FIG. 11, FIG. 12, FIG. 13, FIG. 14, FIG. 15, FIG. 16, FIG. 17, FIG. 18, FIG. 19, FIG. 20, FIG. 21, FIG. 22, FIG. 23, and FIG. 24, in further detail, FIG. 23 shows the programmed operation flow chart 600, which describes the process for the programmed operation of the Pro Plus Neutral Atmosphere and Sanitization Storage Apparatus 1000 or the Refrigerated Neutral Atmosphere and Sanitization Storage Apparatus 1100. First, in the set parameters step 610, the user uses the web application 230 or the mobile application 240; or an application running on a personal computer 770, smart phone 780 or tablet 790 connected through a direct Wi-Fi connection 720 or a direct Bluetooth connection 730 to a direct network server 740; to set the parameters and controls for the Pro Plus Neutral Atmosphere and Sanitization Storage Apparatus 1000 or the Refrigerated Neutral Atmosphere and Sanitization Storage Apparatus 1100, which are communicated to the Pro Plus Neutral Atmosphere and Sanitization Storage Apparatus 1000 or the Refrigerated Neutral Atmosphere and Sanitization Storage Apparatus 1100 through the network servers 210 or direct network servers 740 via a direct Wi-Fi connection 720 or a direct Bluetooth connection 730. Next, in the box response step 620, the Pro Plus Neutral Atmosphere and Sanitization Storage Apparatus 1000 or the Refrigerated Neutral Atmosphere and Sanitization Storage Apparatus 1100 accepts the settings for its parameters and controls from the network servers 210 or direct network servers 740, keeps track of the time, and automatically activates the ozone saturation process at the time scheduled in the settings. For instance, the default setting for the scheduled ozone saturation process may be every 30 days. Next, in the programmed ozone saturation process step 630, the Pro Plus Neutral Atmosphere and Sanitization Storage Apparatus 1000 or the Refrigerated Neutral Atmosphere and Sanitization Storage Apparatus 1100 activates the ozone saturation process. The ozone saturation process comprises turning on a corona ozone generator with an oxygen gas feed and a fan for an amount of time; which are precisely calculated based on the volume of the apparatus, measured temperature and humidity within the insulated airtight enclosure, measure ozone levels within the insulated airtight enclosure, the type and/or weight of the perishable items being sanitized, or the like, and keyed to proprietary tables; or which are determined by custom settings. Next, in the no action step 640, if all system metrics are substantially within their set limits, the Pro Plus Neutral Atmosphere and Sanitization Storage Apparatus 1000 or the Refrigerated Neutral Atmosphere and Sanitization Storage Apparatus 1100 continues to keep time until the next ozone saturation process is scheduled.

The advantages of the present invention include, without limitation, that it provides a method, system and apparatus for storing perishable items that are frequently accessed, which sanitizes the perishable items and reduces their exposure to oxygen and/or temperature and/or humidity so that the perishable items maintain high quality for longer periods of time. The Improved Neutral Atmosphere and Sanitization Storage Apparatus uses ozone generation to prevent parasitic infestation and oxygen degradation of perishable items and may use humidity and temperature control to prevent fungal growth. Additionally, the veneers comprising limestone, mahogany, or a like neutral composite material, which are mounted within the insulated vessel, improve the quality of the perishable items being stored by simulating the conditions of a cave for storing or aging cheese or, similarly, a wine cellar for storing wine while maintaining its quality. Moreover, the present invention's ability to take measurements and relay information to network servers help to identify conditions that would degrade the perishable items being stored as early as possible so that corrective action procedures may be activated to protect the perishable items from degradation.

In broad embodiment, the present invention relates generally to a storage container for storing perishable items that degrade in the presence of oxygen and/or humidity, comprising an openable and insulated storage container, which becomes airtight when closed, and an corona ozone generator with an oxygen gas feed and fan within the airtight enclosure, which converts ambient oxygen trapped within the airtight enclosure into ozone, as well as, methods and systems for the same.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiments, methods, and examples, but by all embodiments and methods that are within the scope and spirit of the invention as claimed.

What is claimed is:

1. An apparatus for storing perishable items that are frequently accessed, said apparatus comprising:
    an outer shell assembly, said outer shell assembly comprising
        an access door, said access door being insulated,
        a remote controlled strike lock, said remote controlled strike lock being able to lock said access door,
        an exposure chamber, said exposure chamber being insulated, said exposure chamber being able to be accessed through said access door and said exposure chamber being airtight when said access door is closed, said exposure chamber comprising:
            veneer panels within said exposure chamber,
        an electronics chamber, said electronics chamber comprising
            a vent to the exterior of said outer shell assembly, and
            an exterior indicator;
    a memory stored in non-transitory computer-readable medium; said memory comprising
        tables of optimal ozone saturation for said perishable items, optimal temperature levels for said perishable items and optimal humidity for said perishable items;
    a processor module, said processor module enclosed within said electronics chamber and said processor module capable of wireless communication, said processor module capable of controlling said remote controlled strike lock to lock or unlock said access door, said processor module comprising said computer-readable medium;
    a power supply module, said power supply module enclosed within said electronics chamber;
    a corona ozone generator, said corona ozone generator enclosed within said exposure chamber, said corona ozone generator being capable of converting ambient oxygen within said exposure chamber into ozone and said corona ozone generator being controllable by said processor module, said corona ozone generator comprising:
        an electric field generator and
        an oxygen gas feed, said oxygen gas feed capable of supplying oxygen gas to said corona ozone generator;
    a perforated basket for storing said perishable items, said perforated basket enclosed within said exposure chamber and said perforated basket being sufficiently perforated to allow substantial air flow around said perishable items stored on said perforated basket;
    a fan, said fan enclosed within said exposure chamber and said fan controllable by said processor module;
    a temperature sensor, said temperature sensor enclosed within said exposure chamber and said temperature sensor being able to send measured temperature data to said processor module;
    a humidity sensor, said humidity sensor enclosed within said exposure chamber and said humidity sensor being able to send measured humidity data to said processor module;
    an ozone sensor, said ozone sensor enclosed within said exposure chamber and said ozone sensor being able to send measured ozone data to said processor module;
    a temperature control unit, said temperature control unit enclosed within said exposure chamber and said temperature control unit controllable by said processor module;
    a humidity control unit, said humidity control unit enclosed within said exposure chamber and said humidity control unit controllable by said processor module;
    wherein
        said apparatus receives said perishable items on to said perforated basket while said access door is open;
        said processor module controls said remote controlled strike lock to lock said access door, thereby making said exposure chamber airtight;
        said processor module receives said measured temperature data from said temperature sensor;
        said processor module receives said measured humidity data from said humidity sensor;
        said processor module receives said measured ozone data from said ozone sensor;
        said processor module accesses said tables in said memory and retrieves a recipe based on said perishable items, said measured temperature data, said measured humidity data and said measured ozone data; and
        said processor module activates said temperature control unit to achieve said optimal temperature for said perishable items; and
        said processor module activates said humidity control unit to achieve said optimal humidity for said perishable items; and said processor module activates said corona ozone generator and said fan, for a time based on retrieved said recipe, to circulate ambient air within said exposure chamber through said corona ozone generator in order to generate ozone within said exposure chamber in an amount sufficient to achieve said optimal ozone saturation and to substantially preserve the quality of said perishable items.

2. An apparatus of claim 1, wherein said humidity control unit comprises a humidifier and a dehumidifier.

3. An apparatus of claim 1, wherein said temperature control unit comprises a Peltier element, said Peltier element being capable of increasing or decreasing the temperature within said exposure chamber in order to maintain a precise temperature range.

4. An apparatus of claim 1, wherein said temperature control unit comprises a refrigerator unit, said refrigerator unit being capable of increasing or decreasing the temperature within said exposure chamber in order to maintain a precise temperature range.

5. An apparatus of claim 1, wherein said veneer panels comprise limestone.

6. An apparatus of claim 1, wherein said veneer panels comprise mahogany.

7. An apparatus of claim 1, wherein said veneer panels comprise a non-reactive composite material.

8. An apparatus of claim 1 further comprising a terpene injector located within said exposure chamber, said terpene injector capable of infusing said perishable items with terpenes, said terpene injector controllable by said processor module.

9. An apparatus of claim 1, wherein said perforated basket comprises a plurality of perforated trays suspended within a cage, said cage comprising
a rigid frame,
a plurality of horizontal u-brackets mounted within said rigid frame,
wherein said perforated trays are supported by said u-brackets.

10. An apparatus of claim 1, said apparatus further comprising
a weight sensor, said weight sensor capable of measuring the weight of said perishable items and said weight sensor being able to send measured weight data to said processor module;
wherein said processor module accesses said tables in said memory and retrieves a recipe based on said measured weight data, in addition to said perishable items, said measured temperature data, said measured humidity data, and said measured ozone data.

11. An apparatus of claim 1, wherein said wireless communication is via Wi-Fi or Bluetooth.

12. An apparatus of claim 1, wherein said processor module connects directly to a network server through said wireless communication.

13. An apparatus of claim 1, wherein said processor module connects to a network server through a wireless device through said wireless communication, said wireless device comprising
a personal computer,
a desktop computer,
a smart phone, or
a tablet.

14. An apparatus of claim 1, wherein said memory is stored on a network server accessible by said processor module using said wireless communication.

15. An apparatus of claim 1, wherein said exterior indicator further comprises a touchscreen, said touchscreen controllable by said processor module.

16. An apparatus of claim 1, wherein said apparatus is self-contained and transportable.

17. A method of storing, curing, and preserving perishable items that are frequently accessed, said method comprising:
obtaining fresh said perishable items;
providing a memory stored in non-transitory computer-readable medium; said memory comprising
tables of optimal ozone saturation for said perishable items, optimal temperature levels for said perishable items and optimal humidity for said perishable items;
providing a processor module, said processor module comprising said memory and said processor module being capable of wireless communication;
enclosing said perishable items on a perforated basket within an insulated airtight container along with a corona ozone generator, an oxygen gas feed, veneer panels, a fan, a temperature sensor, a humidity sensor, an ozone sensor, a temperature control unit, and a humidity control unit; said corona ozone generator, said oxygen gas feed, said temperature control unit, said humidity control unit, and said fan being controllable by said processor module; said temperature sensor being capable of sending measured temperature data to said processor module; said humidity sensor being capable of sending measured humidity data to said processor module; and said ozone sensor being capable of sending measured ozone data to said processor module;
identifying said perishable items to said processor module;
measuring the temperature within said insulated airtight container with said temperature sensor;
sending said measured temperature data to said processor module;
measuring the humidity within said insulated airtight container with said humidity sensor;
sending said measured humidity data to said processor module;
measuring the ozone within said insulated airtight container with said ozone sensor;
sending said measured ozone data to said processor module;
accessing said tables in said memory with said processor module;
converting said measured temperature data, said measured humidity data, and said measured ozone data to a recipe based on said perishable items and said tables with said processor module;
activating said corona ozone generator, said oxygen gas feed, and said fan, using said processor module, for a time based on said recipe;
activating said temperature control unit for a time based on said recipe;
activating said humidity control unit for a time based on said recipe; and
circulating ambient air within said insulated airtight container around said corona ozone generator in order to generate ozone within said airtight container in an amount sufficient to achieve said optimal ozone saturation and to substantially preserve the quality of said perishable items.

18. The method of claim 12, wherein said humidity control unit comprises a humidifier and a dehumidifier.

19. The method of claim 12, wherein said temperature control unit comprises a Peltier element, said Peltier element being capable of increasing or decreasing the temperature within said insulated airtight chamber in order to maintain a precise temperature range.

20. The method of claim 12, wherein said temperature control unit comprises a refrigerator unit, said refrigerator unit being capable of increasing or decreasing the temperature within said insulated airtight chamber in order to maintain a precise temperature range.

21. The method of claim 12, wherein said veneer panels comprise limestone.

22. The method of claim 12, wherein said veneer panels comprise mahogany.

23. The method of claim 12, wherein said veneer panels comprise a non-reactive composite material.

24. The method of claim 12, further comprising locating a terpene injector within said insulated airtight chamber, said terpene injector capable of infusing said perishable items with terpenes and said terpene injector controllable by said processor module, and infusing said perishable items with terpenes.

25. The method of claim 12, said method further comprising
enclosing a weight sensor within said insulated airtight container, said weight sensor capable of measuring the weight of said perishable items and said weight sensor being able to send measured weight data to said processor module;
measuring the weight of said perishable items with said weight sensor;
sending said measured weight data to said processor module;
converting said measured weight data, along with said measured temperature data said measured humidity data, and said ozone data, to a recipe based on said perishable items and said tables;
wherein said processor module accesses said tables in said memory and retrieves said recipe based on said measured weight data, in addition to said perishable items, said measured temperature data, and said measured humidity data.

26. The method of claim 12, wherein said wireless communication is via Wi-Fi or Bluetooth.

27. The method of claim 12, wherein said processor module connects directly to a network server through said wireless communication.

28. The method of claim 12, wherein said processor module connects to a network server through a wireless device through said wireless communication, said wireless device comprising
a personal computer,
a desktop computer,
a smart phone, or
a tablet.

29. The method of claim 12, wherein said memory is stored on a network server accessible by said processor using said wireless communication.

30. A system for storing, curing, and preserving perishable items that are frequently accessed, said system comprising:
said perishable items;
an apparatus of claim 1;
a wireless device, said wireless device comprising
a personal computer,
a desktop computer,
a smart phone, or
a tablet;
a network server, said network server accessible by said apparatus and by said wireless device;
wherein said apparatus is set up and initially configured by
activating said apparatus using an application running on said wireless device or a manual switch on said apparatus,
connecting said apparatus to said network server using said application,
registering said apparatus on said network servers using said application,
loading default settings for said apparatus and tracking default alerts for variations from said default settings, when said default settings are selected by a user, and
configuring custom settings and tracking custom alerts for variations from said custom settings, when said custom settings are selected by said user;
wherein said apparatus interacts with said application by
pinging said apparatus with said network server,
sending a response from said apparatus to said network server with updated tracking parameters for said apparatus,
sending said tracking parameters to said application on said wireless device for access and viewing by said user,
generating an alert when said tracking parameters fall outside said default settings or said custom settings, and
adjusting said custom settings by accessing said application on said wireless device, when dictated by said alert, and updating said custom settings on said apparatus until said alert is cleared;
wherein said apparatus is manually operated by
opening said apparatus;
placing said perishable items within said apparatus;
closing said apparatus;
using said application to connect to said network servers and to activate a user-mandated hard cycle,
receiving said activation of said user-mandated hard cycle on said network server,
in response to said network servers, activating the temperature control process, said temperature control process comprising activating said temperature control unit and said fan for an amount of time, which is precisely calculated based on the volume of said apparatus, the type and/or weight of said perishable items being sanitized and keyed to said tables, or which are determined by said custom settings,
in response to said network servers, activating the humidity control process, said humidity control process comprising activating said humidity control unit and said fan for an amount of time, which is precisely calculated based on the volume of said apparatus, the type and/or weight of said perishable items being sanitized and keyed to said tables, or which are determined by said custom settings,
in response to said network servers, activating the ozone saturation process, said ozone saturation process comprising turning on said corona ozone generator and said fan for an amount of time, which is precisely calculated based on the volume of said apparatus, the type and/or weight of said perishable items being sanitized and keyed to said tables, or which are determined by said custom settings, and completing said temperature control process, said humidity control process, and said ozone saturation process and entering a rest cycle until a new batch of said perishable items is available for sanitation; and wherein said apparatus undergoes programmed operation by using said application to set said tracking parameters and controls for said apparatus, accepting said tracking parameters and controls on said apparatus, automatically activating said temperature control process at the time scheduled by said controls, said temperature control process comprising activating said temperature control unit and said fan for an amount of time, which is precisely calculated based on the volume of said apparatus, the type and/or weight of said perishable items being sanitized and keyed to said tables, or which are determined by said custom settings, automatically activating said humidity control process at the time scheduled by said controls, said humidity control process comprising activating said humidity control unit and said fan for an amount of time, which is precisely calculated based on the volume of said apparatus, the type and/or weight of said perishable items being sanitized and keyed to said tables, or which are determined by said custom settings, automatically activating said ozone saturation process at the time scheduled by said controls, said ozone saturation process comprising turning on said corona ozone generator and said fan for an amount of time; which is precisely calculated based on said volume of said apparatus, said type and/or said weight of said perishable items being sanitized and keyed to said tables, or which are determined by said custom settings, and keeping time on said apparatus until the next said temperature control process, said humidity control process, or said ozone saturation process is scheduled.

* * * * *